United States Patent
Ni et al.

(10) Patent No.: US 12,332,330 B2
(45) Date of Patent: Jun. 17, 2025

(54) SYSTEMS AND METHODS FOR DIAGNOSIS AND IMAGE GUIDED THERAPY WITH SUPERCONDUCTING MAGNET SHIELDING AND PROVIDING HEAT EXCHANGE

(71) Applicant: SHANGHAI UNITED IMAGING HEALTHCARE CO., LTD., Shanghai (CN)

(72) Inventors: Cheng Ni, Shanghai (CN); Xingen Yu, Shanghai (CN); Peng Wang, Shanghai (CN); Jianfeng Liu, Shanghai (CN); Wei Han, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 329 days.

(21) Appl. No.: 17/179,429

(22) Filed: Feb. 19, 2021

(65) Prior Publication Data

US 2021/0255262 A1      Aug. 19, 2021

(30) Foreign Application Priority Data

Feb. 19, 2020   (CN) .......................... 202010103170.8
Mar. 6, 2020    (CN) .......................... 202010151063.2

(51) Int. Cl.
*G01R 33/34*    (2006.01)
*A61B 5/055*    (2006.01)

(52) U.S. Cl.
CPC ........ *G01R 33/34023* (2013.01); *A61B 5/055* (2013.01); *G01R 33/3403* (2013.01)

(58) Field of Classification Search
CPC .......... A61N 2005/1094; A61N 5/1077; A61N 5/10; A61N 2005/1055; A61N 5/00
See application file for complete search history.

(56) References Cited

U.S. PATENT DOCUMENTS 5,550,383 A * 8/1996 Haskell ..................... C08K 3/08
                                                    250/519.1
6,147,844 A   11/2000 Huang et al.
6,172,588 B1  1/2001 Laskaris et al.
(Continued)

FOREIGN PATENT DOCUMENTS

CN      105233425 A    1/2016
CN      106531396 A    3/2017
(Continued)

OTHER PUBLICATIONS

First Office Action in Chinese Application No. 202010151063.2 mailed on Apr. 6, 2021, 19 pages.
(Continued)

*Primary Examiner* — Serkan Akar
(74) *Attorney, Agent, or Firm* — METIS IP LLC

(57) ABSTRACT

A system may comprise a magnetic resonance imaging (MRI) device including a bore that is configured to accommodate a subject. The MRI device may include multiple superconducting magnets configured to generate a magnetic field in the bore. The MRI device may include one or more superconducting connections each of which is configured to connect at least two of the multiple superconducting magnets. The system may further include a radiation source configured to emit a radiation beam toward the bore. The radiation source may be able to rotate in a plane perpendicular to a direction of the magnetic field in the bore. The MRI device may further include one or more protection components configured to prevent at least a portion of the radiation beam from irradiating the one or more superconducting connections.

19 Claims, 15 Drawing Sheets

(56) References Cited

U.S. PATENT DOCUMENTS

| | | |
|---|---|---|
| 2002/0196020 A1 | 12/2002 | Dean et al. |
| 2005/0062473 A1 | 3/2005 | Ryan et al. |
| 2010/0231215 A1* | 9/2010 | Ma .................... G01R 33/3804 324/318 |
| 2011/0218420 A1 | 9/2011 | Carlone et al. |
| 2013/0203603 A1 | 8/2013 | Harrison |
| 2014/0135615 A1 | 5/2014 | Kruip |
| 2014/0253125 A1 | 9/2014 | Sakakura et al. |
| 2016/0233011 A1 | 8/2016 | Eguchi |
| 2016/0256712 A1 | 9/2016 | Vahala et al. |
| 2016/0263400 A1 | 9/2016 | Calvert |
| 2016/0356869 A1 | 12/2016 | Dempsey et al. |
| 2018/0051852 A1 | 2/2018 | Wikus et al. |
| 2019/0060670 A1 | 2/2019 | Ni et al. |
| 2019/0265315 A1 | 8/2019 | Bandara et al. |
| 2021/0080527 A1 | 3/2021 | Wang et al. |

FOREIGN PATENT DOCUMENTS

| | | |
|---|---|---|
| CN | 206293236 U | 6/2017 |
| CN | 107754099 A | 3/2018 |
| CN | 111228658 A | 6/2020 |
| CN | 111330167 A | 6/2020 |
| GB | 2545436 A | 6/2017 |
| JP | 2008130947 A | 6/2008 |
| JP | 5155807 B2 | 12/2012 |
| JP | 2017204552 A | 11/2017 |
| WO | 2015189786 A1 | 12/2015 |

OTHER PUBLICATIONS

First Office Action in Chinese Application No. 202010103170.8 mailed on Mar. 10, 2021, 14 pages.

* cited by examiner

SYSTEMS AND METHODS FOR DIAGNOSIS AND IMAGE GUIDED THERAPY WITH SUPERCONDUCTING MAGNET SHIELDING AND PROVIDING HEAT EXCHANGE

CROSS-REFERENCE TO RELATED APPLICATIONS

This application claims priority to Chinese Patent Application No. 202010103170.8 filed on Feb. 19, 2020, and Chinese Patent Application No. 202010151063.2 filed on Mar. 6, 2020, the contents of each of which are hereby incorporated by reference.

TECHNICAL FIELD

The present disclosure generally relates radiotherapy treatment, and more particular, to a medical system for image guided radiotherapy.

BACKGROUND

Various imaging techniques have been widely used in medical diagnosis, radiation therapy planning, surgery planning and other medical procedures, such as an X-ray photography, a magnetic resonance imaging (MRI), a computed tomography (CT), a positron emission tomography (PET), etc. Using an image guided radiotherapy technique, an imaging device (e.g., an MRI device) cannot imaging the subject when a radiotherapy device (e.g., a linear accelerator) performs radiotherapy treatment. For example, when a radiotherapy device and an MRI device are working at the same time, radiation beams emitted by the radiotherapy device may irradiate certain parts of the MRI device, which may cause a superconducting magnet of the MRI device to loss superconductivity, thereby resulting in abnormal MRI. Therefore, it is desirable to develop systems and methods for image guided radiotherapy with improved efficiency and reliability.

SUMMARY

According to an aspect of the present disclosure, a system is provided. The system may comprise a magnetic resonance imaging (MRI) device including a bore that is configured to accommodate a subject. The MRI device may include multiple superconducting magnets configured to generate a magnetic field in the bore and one or more superconducting connections each of which is configured to connect at least two of the multiple superconducting magnets. The system may also include a radiation source configured to emit a radiation beam toward the bore, the radiation source may be able to rotate in a plane perpendicular to a direction of the magnetic field. The MRI device may further include one or more protection components configured to prevent at least a portion of the radiation beam from irradiating the one or more superconducting connections.

In some embodiments, at least one of the protection components may include a tubular structure, and one of the one or more superconducting connections may be arranged in the tubular structure.

In some embodiments, at least one of the protection components may include a material with an attenuation coefficient exceeding a threshold.

In some embodiments, at least one of the protection components may include a material with a thermal conductivity less than a threshold.

In some embodiments, a direction of the radiation beam may be perpendicular to the direction of the magnetic field.

In some embodiments, the radiation source may include a treatment radiation source in a radiotherapy device.

In some embodiments, the radiotherapy device may include a gantry, the radiation source may be mounted on the gantry, and the radiation source may rotate in the plane perpendicular to the direction of the magnetic field with a rotation of the gantry.

In some embodiments, a cooling assembly may be configured to cool the one or more superconducting magnets, the cooling assembly may include one or more refrigerators and one or more heat conductors physically connecting the one or more refrigerators and the one or more superconducting magnets.

In some embodiments, space may be formed between the one or more superconducting magnets, at least a portion of the radiation source may be located in the space, and the radiation source may be able to rotate in the plane perpendicular to a direction of the magnetic field in the space.

According to another aspect of the present disclosure, a system may be provided. The system may include a magnetic resonance imaging (MRI) device. The MRI device may include a main body including a bore that is configured to accommodate a subject, one or more superconducting magnets around the bore being configured to generate a magnetic field in the bore, a cooling assembly configured to cool the one or more superconducting magnets without immersing the one or more superconducting magnets in a coolant. The cooling assembly may include one or more refrigerators and one or more heat conductors thermally connecting the one or more refrigerators and the one or more superconducting magnets. The system may further include a radiation source configured to emit a radiation beam toward the bore. The radiation source may be able to simultaneously rotate with a rotation of the MRI device.

In some embodiments, the main body may further include a channel on a shell of the main body along a direction substantially perpendicular to a direction of the magnetic field, and at least a portion of the radiation source disposed in the channel, the radiation beam may pass through the channel to the bore.

In some embodiments, the shell of the main body may include an inner wall and an outer wall, the outer wall may be configured with a first through hole and the inner wall may be configured with a second through hole, and a diameter of the first through hole may exceed a diameter of the second through hole, the channel may be formed by the first through hole and the second through hole.

In some embodiments, each of the superconducting magnets may include a main coil and a shielding coil, the main coils of the superconducting magnets may be electrically connected via one or more first superconducting connections, and the shielding coils of the superconducting magnets may be electrically connected by one or more second superconducting connections.

In some embodiments, the one or more refrigerators may include one single refrigerator that is thermally connected with the main coil and the shielding coil of one of the superconducting magnets via one of the heat conductors, the main coils of the superconducting magnets may thermally connect.

In some embodiments, the main coils of the superconducting magnets may thermally connect; the shielding coils of the superconducting magnets may thermally connect; and the main coil and the shielding coil of another one of the superconducting magnets may thermally connect via one of the heat conductors.

In some embodiments, a count of the one or more refrigerators may equal 2, and each of the one or more refrigerators may thermally connected with the main coil and the shielding coil in one of the one or more superconducting magnets through one of the one or more heat conductors.

In some embodiments, the MRI device may include one or more protection components each of which is configured to prevent at least a portion of the radiation beam from irradiating at least one of the one or more first superconducting connections or the one or more second superconducting connections.

In some embodiments, one of the one or more heat conductors may be made of a metal material, and a thermal conductivity of the metal material exceeds a threshold.

In some embodiments, the radiation source may include a treatment radiation source in a radiotherapy device, and the MRI device may be configured to obtain images of the subject while the radiotherapy device is performing radiotherapy treatment.

In some embodiments, the system may further comprise a processor, and the processor may be configured to obtain image data collected by the MRI device; and control the radiotherapy device to perform the radiotherapy treatment based on the image data.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
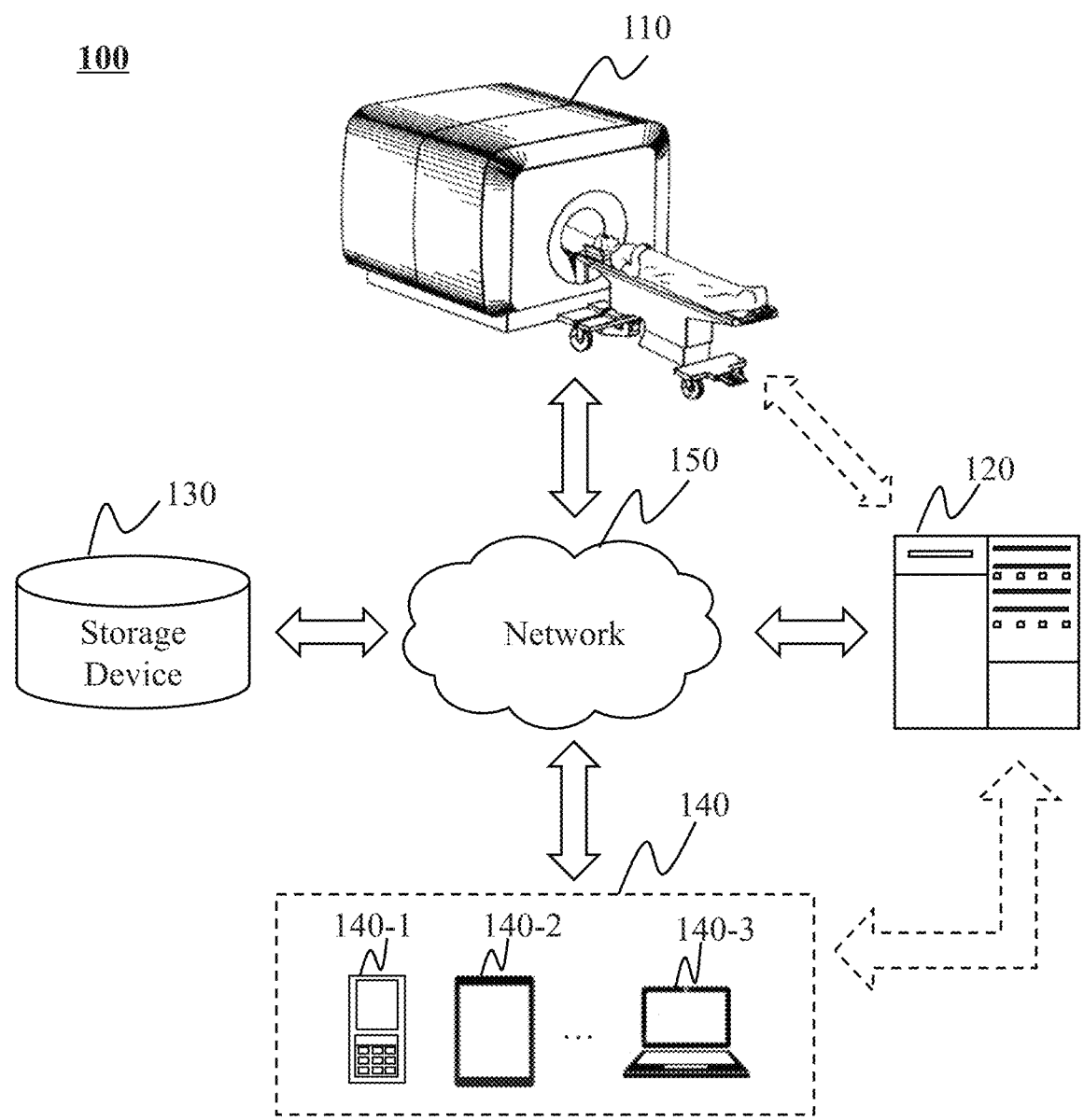
FIG. 1 is a schematic structural diagram illustrating an exemplary medical system according to some embodiments of the present disclosure.

In order to illustrate the technical solutions related to the embodiments of the present disclosure, brief introduction of the drawings referred to the description of the embodiments is provided below. Obviously, drawings described below are only some examples or embodiments of the present disclosure. Those having ordinary skills in the art, without further creative efforts, may apply the present disclosure to other similar scenarios according to these drawings. Unless apparent from the locale or otherwise stated, like reference numerals represent similar structures or operation throughout the several views of the drawings.

It will be understood that the term "system," "device," "unit," and/or "module" used herein are one method to distinguish different components, elements, parts, section or assembly of different level in ascending order. However, if other words may achieve the same purpose, the words may be replaced by other expressions.

As used in the disclosure and the appended claims, the singular forms "a," "an," and "the" include plural referents unless the content clearly dictates otherwise. In general, the terms "comprise," "comprises," and/or "comprising," "include," "includes," and/or "including," merely prompt to include steps and elements that have been clearly identified, and these steps and elements do not constitute an exclusive listing. The methods or devices may also include other steps or elements.

Although this specification makes various references to certain modules or units in the system according to the embodiments of the specification, any number of different modules or units may be used and run on the client and/or server. These modules are only used for illustration purposes, and different modules may be used in different aspects of the system and method.

FIG. 1 is a schematic diagram illustrating an exemplary medical system according to some embodiments of the present disclosure. Merely by way of example, as illustrated in FIG. 1, the medical system 100 may include a medical device 110, a processing device 120, a storage device 130, one or more terminals 140, and a network 150. In some embodiments, the components in the medical system 100 may be connected to and/or communicate with each other in one or more of various ways. Merely by way of example, the medical device 110 may be connected to the processing device 120 through the network 150. As another example, medical device 110 may be connected to the processing device 120 directly as illustrated in FIG. 1. As a further example, the terminal(s) 140 may be connected to another component of the medical system 100 (e.g., the processing device 120) via the network 150. As still a further example, the terminal(s) 140 may be connected to the processing device 120 directly as illustrated by the dotted arrow in FIG. 1. As still a further example, the storage device 130 may be connected to another component of the medical system 100 (e.g., the processing device 120) directly as illustrated in FIG. 1, or through the network 150.

The medical device 110 may include a multi-modality device. In some embodiments, the multi-modality device may be configured to acquire image data of different modalities. For example, the multi-modality device may include a first device and a second device each of which is configured to provide image data including a representation of at least one part of a subject. In some embodiments, the first device may be configured to generate a magnetic field in the acquisition of first image data. For example, the first device may include a magnetic resonance spectroscopy (MRS) device, a magnetic resonance imaging (MRI) device (also referred to as an MR device, an MR scanner), etc. The second device may include an imaging radiation source that is configured to generate and emit radiation beams to irradiate the subject in the acquisition of second image data. For example, the second device may include an X-ray imaging device, a computed tomography (CT) scanner, a digital radiography (DR) scanner (e.g., a mobile digital radiography), a digital creast tomosynthesis (DBT) scanner, a digital subtraction angiography (DSA) scanner, a dynamic spatial reconstruction (DSR) scanner, an X-ray microscopy scanner. In some embodiments, the image data relating to at least one part of a subject may include an image (e.g., an image slice), projection data, or a combination thereof. For example, the image data of the subject may include a scout image associated with a body part of the subject. In some embodiments, the image data may be a two-dimensional (2D) imaging data, a three-dimensional (3D) imaging data, a four-dimensional (4D) imaging data, or the like, or any combination thereof. The subject accommodated in the bore of the MRI device may be biological or non-biological. For example, the subject may include a patient, a man-made object, etc. As another example, the subject may include a specific portion, organ, tissue, and/or a physical point of the patient. Merely by way of example, the subject may include head, brain, neck, body, shoulder, arm, thorax, cardiac, stomach, blood vessel, soft tissue, knee, feet, or the like, or a combination thereof.

In some embodiments, the multi-modality device may be configured to acquire image data relating to at least one part of a subject and perform treatment on the at least one part of the subject, etc. For example, the multi-modality device may include a first device configured to generate an image including a representation of at least one part of a subject and a second device configured to perform a treatment on at least one part of the subject. The first device may include a magnetic resonance spectroscopy (MRS) device, a magnetic resonance imaging (MRI) device (also referred to as an MR device, an MR scanner), etc. The second device may include a treatment device. The treatment device may include a treatment radiation source that is configured to generate and emit radiation beams to irradiate the subject in the treatment. Exemplary treatment devices may include a radiotherapy device (e.g., a linear accelerator), an X-ray treatment device, etc.

The following descriptions are provided regarding a multi-modality device including an MRI device and a radiotherapy device as the medical device 110 unless otherwise stated. It should be noted that the descriptions of the MRI device and the radiotherapy device in the present disclosure are merely provided for illustration, and not intended to limit the scope of the present disclosure. More descriptions for the multi-modality device may be found elsewhere in the present disclosure (e.g., FIGS. 2-5 and the descriptions thereof).

The processing device 120 may process data and/or information obtained from the medical device 110, the terminal(s) 140, and/or the storage device 130. For example, the processing device 120 may be configured to obtain image data collected by the medical device 110 (e.g., an imaging device of the medical device 110). As another example, the processing device 120 may be configured to control the medical device 110 (e.g., a radiotherapy device of the medical device 110) to perform radiotherapy treatment based on the image data.

In some embodiments, the processing device 120 may be a computer, a user console, a single server or a server group, etc. The server group may be centralized or distributed. In some embodiments, the processing device 120 may be local or remote. For example, the processing device 120 may access information and/or data stored in the medical device 110, the terminal(s) 140, and/or the storage device 130 via the network 150. As another example, the processing device 120 may be directly connected to the medical device 110, the terminal(s) 140 and/or the storage device 130 to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

The storage device 130 may store data, instructions, and/or any other information. In some embodiments, the storage device 130 may store data obtained from the terminal(s) 140 and/or the processing device 120. For example, the storage device 130 may store image data (e.g., MRI images) collected by the medical device 110. As another example, the storage device 130 may store one or more algorithms for processing the image data, e.g., a magnetic resonance image reconstruction algorithm for MR image reconstruction, etc. In some embodiments, storage device 130 may store data and/or instructions that the processing device 120 may execute or use to perform exemplary methods/systems described in the present disclosure. In some embodiments, the storage device 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the medical system 100 (e.g., the terminal(s) 140, the processing device 120, etc.). One or more components in the medical system 100 may access the data or instructions stored in the storage device 130 via the network 150. In some embodiments, the storage device 130 may be directly connected to or communicate with one or more other components in the medical system 100 (e.g., the processing device 120, the terminal(s) 140, etc.). In some embodiments, the storage device 130 may be part of the processing device 120 or the medical device 110.

In some embodiments, a user and/or an operator may operate the medical system 100 using the terminal(s) 140. The terminal(s) 140 may include a mobile device 140-1, a tablet computer 140-2, a laptop computer 140-3, or the like, or any combination thereof. In some embodiments, the mobile device 140-1 may include a smart home device, a wearable device, a mobile device, a virtual reality device, an augmented reality device, or the like, or any combination thereof. In some embodiments, the smart home device may include a smart lighting device, a control device of an intelligent electrical device, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 140 may be part of the processing device 120.

The network 150 may include any suitable network that can facilitate the exchange of information and/or data for the medical system 100. In some embodiments, one or more components of the medical device 110, the magnetic resonance imaging device (e.g., an MR device, etc.), the terminal(s) 140, the processing device 120, the storage device 130, etc., may communicate information and/or data with one or more other components of the medical system 100 via the network 150. For example, the processing device 120 may obtain data from the medical device 110 via the network 150. As another example, the processing device 120 may obtain user instructions from the terminal(s) 140 via the network 150. The network 150 may be and/or include a public network (e.g., the Internet), a private network (e.g., a local area network (LAN), a wide area network (WAN), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the medical system 100 may be connected to the network 150 to exchange data and/or information.

It should be noted that the above description of the medical system 100 is merely provided for the purposes of illustration, and not intended to limit the scope of the present disclosure. For persons having ordinary skills in the art, multiple variations and modifications may be made under the teachings of the present disclosure. For example, the assembly and/or function of the medical system 100 may be varied or changed according to specific implementation scenarios.

Figure 2:
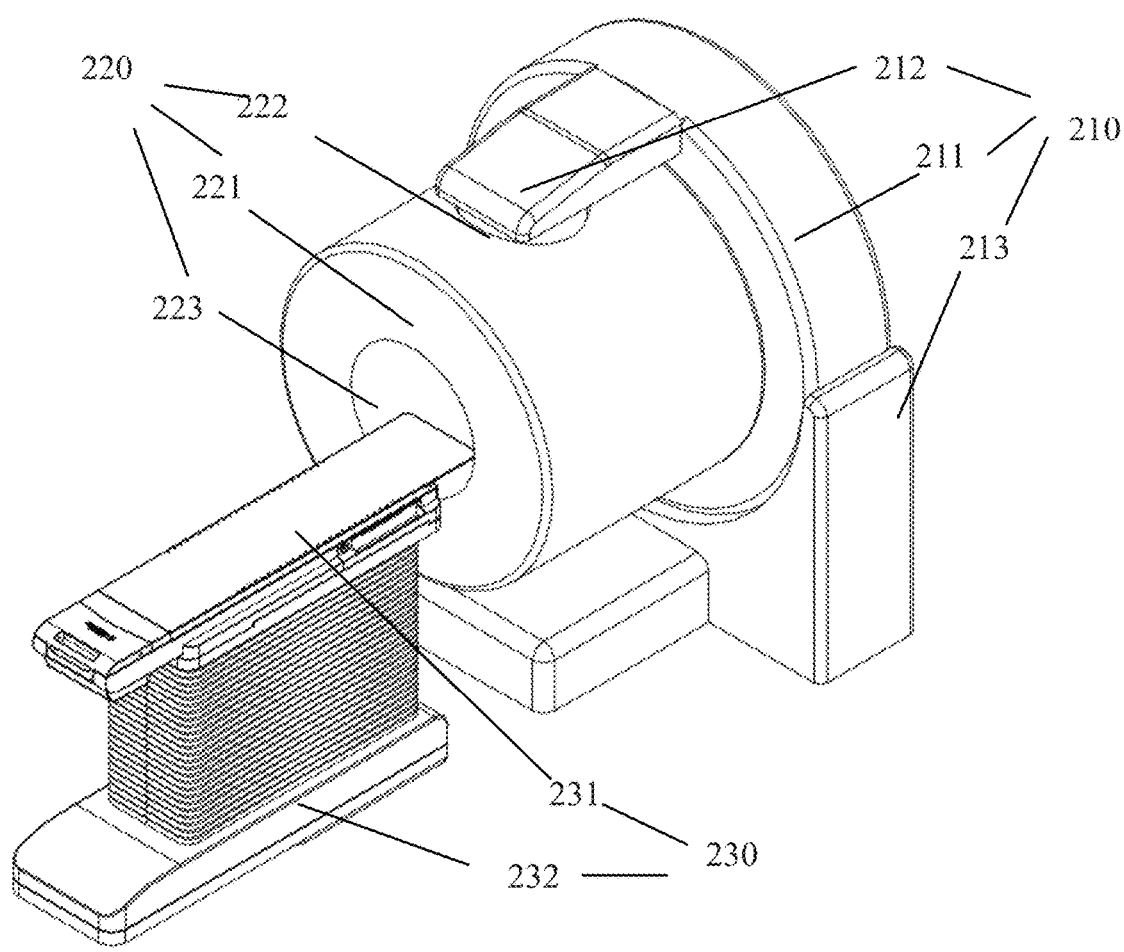
FIGS. 2-4 are schematic diagrams illustrating an exemplary medical device according to some embodiments of the present disclosure.
Figure 3:
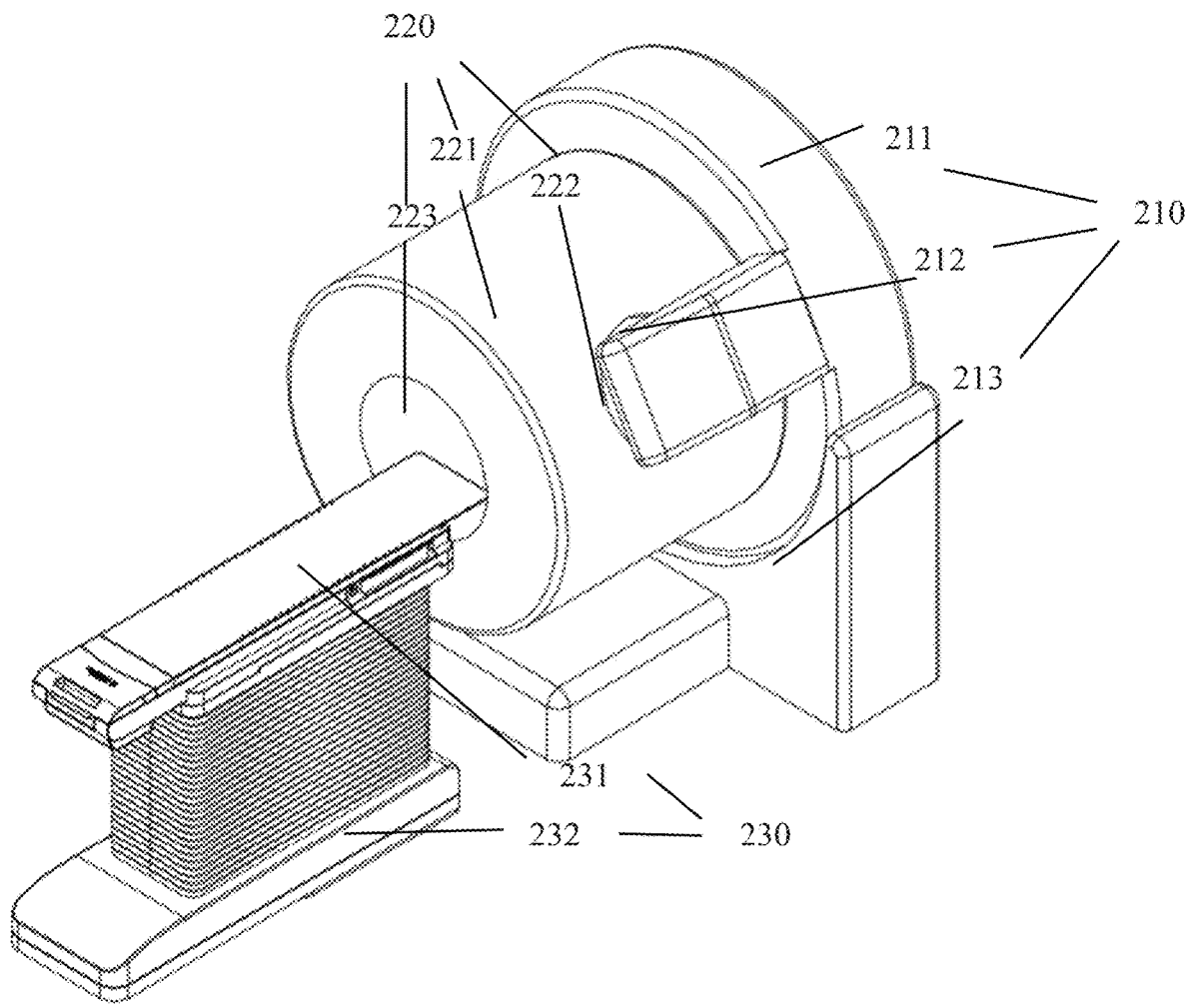
Figure 4:
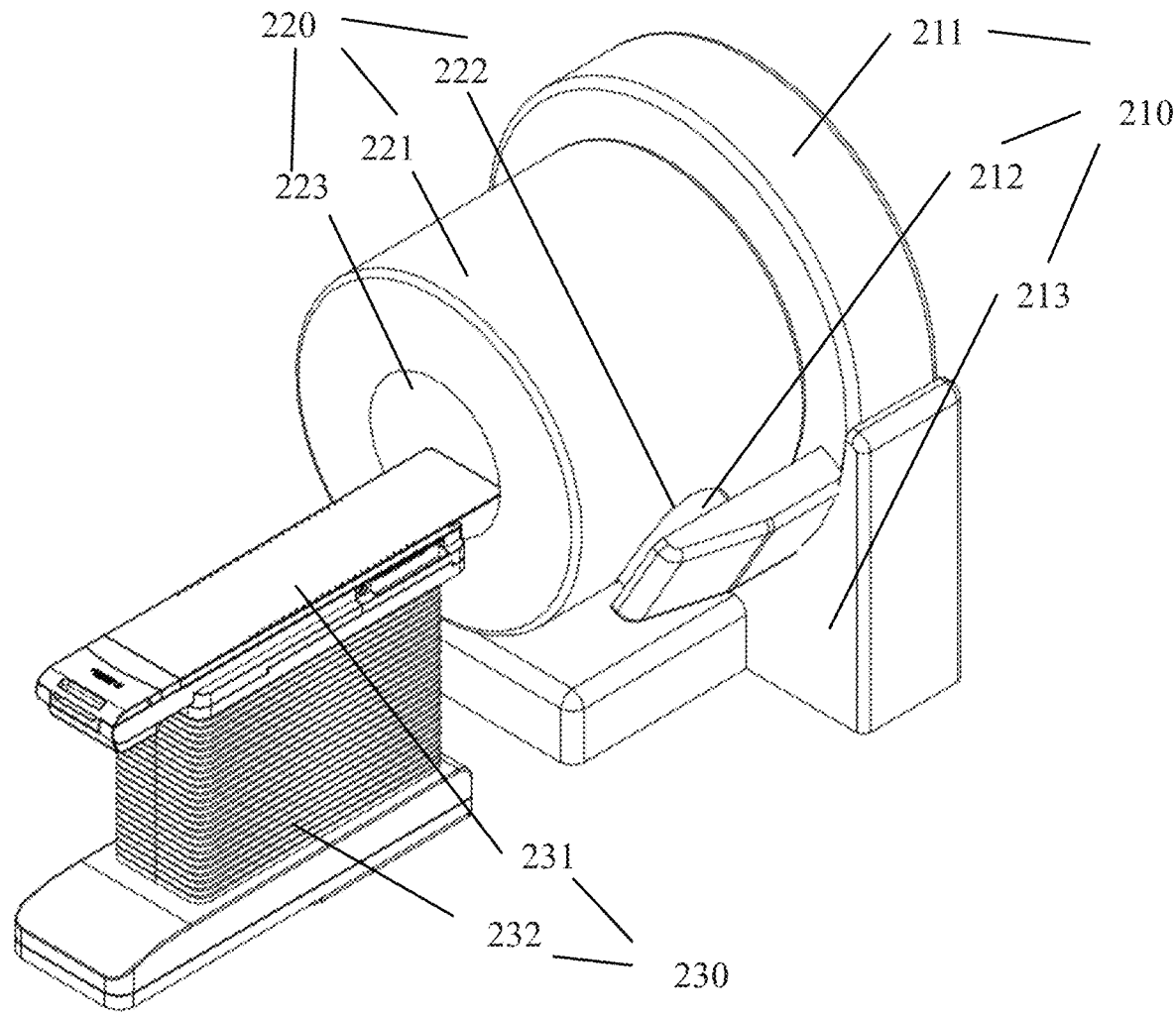

FIGS. 2-4 are schematic diagrams illustrating an exemplary medical device according to some embodiments of the present disclosure. In some embodiments, the medical device 200 may be an exemplary embodiment of the medical device 110. In some embodiments, the medical device 200 may include a multi-modality device. The following descriptions are provided regarding the multi-modality device including an MRI device and a radiotherapy device unless otherwise stated. It should be noted that the descriptions of the MRI device and the radiotherapy device in the present disclosure are merely provided for illustration, and not intended to limit the scope of the present disclosure.

The medical device 200 may include a radiotherapy device 210, an MRI device 220, and a couch 230.

The radiotherapy device 210 may be configured for treatment, for example, performing a radiotherapy treatment on a subject. The radiotherapy device 210 may include a cyclotron, an induction accelerator, a linear accelerator (LINAC), etc. For example, the radiotherapy device 210 may include a linear accelerator (LINAC) that is configured for irradiating a subject (e.g., tumors in a patient) by accelerating electrons, ions, and/or protons.

The radiotherapy device 210 may include a gantry 211, a treatment head 212, and a base 213. The treatment head 212 may be mounted on the gantry 211. The gantry 211 may be mounted on and supported by the base 213. The treatment head 212 may be configured to generate and emit radiation beams for radiotherapy treatment. In some embodiments, the treatment head 212 may include a radiation source configured to generate and emit radiation beams. The radiation beams may include X-ray beams, electron beams, gamma ray beams, a proton ray beams, etc.

The MRI device 220 may be configured to obtain image data relating to one part of a subject. In some embodiments, the radiotherapy device 210 may be configured to perform radiotherapy treatment based on the image data acquired by the MRI device 220.

In some embodiments, the MRI device 220 may include a main body 221. The main body 221 of the MRI device 220 may include a bore 223 that is configured to accommodate a subject. The main body 221 may include a shell for supporting and/or carrying parts of the MRI device 220 (e.g., a superconducting magnet, etc.). The MRI device 220 may scan a subject located within the bore 223 and generate image data relating to the subject. In the present disclosure, "subject" and "object" are used interchangeably. In some embodiments, the subject may be accommodated in the bore 223 to receive radiotherapy treatment performed by the radiotherapy device 210. The treatment head 212 may emit radiation rays toward the bore 223 of the MRI device 220 to perform radiotherapy treatment.

In some embodiments, the MRI device 220 may include a magnet assembly, a gradient coil assembly, and a radiofrequency (RF) coil assembly. The magnet assembly of the MRI device 220 may include one or more superconducting magnets arranged around the bore 223.

The one or more superconducting magnets may generate a first magnetic field (also referred to as a main magnetic field) for polarizing the subject to be scanned. The one or more superconducting magnets may include a permanent magnet, a superconducting electromagnet, a resistive electromagnet, etc. In some embodiments, the superconducting magnets may include superconducting coils to generate the main magnetic field under a low working temperature, for example, lower than 25 Kelvin, or lower than 15 Kelvin, or lower than 4.5 Kelvin, etc. For example, the one or more superconducting magnets may include one or more main coils and one or more shielding coils. More descriptions for the main coils and shielding coils may be found elsewhere in the present disclosure, see FIG. 6 and relevant descriptions.

The gradient coil assembly may generate a second magnetic field (also referred to as a gradient magnetic field). The gradient coil assembly may include X-gradient coils, Y-gradient coils, and Z-gradient coils. The gradient coil assembly may generate one or more magnetic field gradient pulses to the main magnetic field in the X direction (Gx), the Y direction (Gy), and the Z direction (Gz) to encode the spatial information of the subject. In some embodiments, the X-direction may be designated as a frequency encoding direction, while the Y-direction may be designated as a phase encoding direction. The Z-direction may be perpendicular to a plane formed by the X-direction and the Y direction. As used herein, the Z-direction may be substantially parallel with the direction of the main magnetic field generated by the superconducting magnets in the bore 223. The main magnetic field generated by the superconducting magnet in the bore 223 may be substantially parallel with an extension direction (also referred to as a long axis direction) of the bore 223. The RF coil assembly may include a plurality of RF coils. The RF coils may include one or more RF transmit coils and/or one or more RF receiver coils. The RF transmit coil(s) may transmit RF pulses to the subject. The RF receiver coils may receive MR signals from the subject.

In some embodiments, the MRI device 220 may further include a gantry supporting the main body 221 that is different from the gantry 211 of the radiotherapy device 210. In some embodiments, the MRI device 220 may further include a base where the gantry of the MRI device 220 is mounted on. In some embodiments, the MRI device 220 and the radiotherapy device 210 may be mounted on the same gantry (e.g., the gantry 221).

In some embodiments, the magnet assembly may include a cryostat. The cryostat may include a coolant (e.g., liquid helium) configured to keep the one or more superconducting magnets that are located in the cryostat under a low working temperature (e.g., approximately 4.2 K) so that the one or more superconducting magnets accommodated in the cryostat may stay in the superconducting state. The cryostat may include an outer vessel, a thermal shield, and an inner vessel. More descriptions for the superconducting magnets and the cryostat may be found elsewhere in the present disclosure (e.g., FIG. 11 and the descriptions thereof).

In some embodiments, the radiation source of the treatment head 212 may be able to rotate relative to the MRI device 220 while the MRI device 220 is immobilized. In some embodiments, the radiation source of the treatment head 212 may be able to rotate in a plane perpendicular to a direction of the main magnetic field generated by one or more superconducting magnets. The radiation beams generated by the radiation source of the treatment head 212 may be emitted toward the bore 223 through the space between two connected superconducting magnets. The direction of the radiation beams may be substantially perpendicular to the direction of the main magnetic field. In some embodiments, the magnet assembly may include one or more superconducting connections each of which is configured to connect at least two of the one or more superconducting magnets. In some embodiments, main coils may be connected via one or more first superconducting connections. In some embodiments, shielding coils may be connected via one or more second superconducting connections. In some embodiments, at least one of the main coils may be connected with at least one of the shielding coils via one or more third superconducting connections (not shown). More descriptions for the superconducting connections may be found elsewhere in the present disclosure. Space may be formed between two connected superconducting magnets. In some embodiments, the magnet assembly may include one or more protection components configured to prevent at least a portion of radiation beams to irradiate the superconducting connections. For example, the one or more protection components may absorb at least a portion of radiation beams when the radiation beams transmit toward the one or more superconducting connections. In some embodiments, each of the one or more superconducting connections may be located in one of the one or more protection components. More descriptions for the one or more superconducting connections and one or more protection components may be found elsewhere in the present disclosure (e.g., FIGS. 11-15 and the descriptions thereof).

In some embodiments, the radiation source of the treatment head 212 may be able to simultaneously rotate with the MRI device 220 along a rotation axis of the MRI device 220. The rotation axis of the MRI device 220 may be parallel with the direction of the main magnetic field generated by the one or more superconducting magnets or the long axis of the bore 223. For example, the MRI device 220 and the radiotherapy device 210 may be mounted on the same gantry 211. The MRI device 220 and the radiotherapy device 210 may simultaneously rotate along with a rotation of the gantry 211. In some embodiments, the magnet assembly may include a cooling assembly that is configured to cool the superconducting magnets (e.g., one or more main coils and one or more shielding coils) without using a coolant (e.g., liquid helium) to guarantee the superconducting magnets stays in a superconducting state. The cooling assembly may include one or more refrigerators and one or more heat conductors physically connecting the one or more refrigerators and the superconducting magnets. Heat generated by the superconducting magnets may be conducted to the one or more refrigerators by the one or more heat conductors. As used herein, using the cooling assembly to cool the superconducting magnets (e.g., one or more main coils and one or more shielding coils) without using a coolant also referred to as a coolant free cooling technique. The coolant free cooling technique refers to that the superconducting magnets are cooled without immersing the superconducting magnets in a coolant (e.g., liquid helium). More descriptions for the cooling assembly may be found elsewhere in the present disclosure (e.g., FIGS. 7-8 and the descriptions thereof).

In some embodiments, at least a portion of the radiotherapy device 210 (e.g., the treatment head 212) may be located in the main body 221. For example, the main body 221 of the MRI device 220 may include a channel 222 (or a grove) on a shell of the main body 221 along a direction substantially perpendicular to the long axis direction (also referred to as an axial direction) of the bore 223, and at least a portion of the radiation source of the treatment head 212 may be disposed in the channel 222. The radiation source of the treatment head 212 may be positioned in the channel 222 such that radiation beams generated by the radiation source of the treatment head 212 may be transmitted to the bore 223. In some embodiments, the directions of the radiation beams generated by the radiation source of the treatment head 212 may be substantially perpendicular to the direction of the magnetic field generated by the MRI device 220. In some embodiments, the channel 222 may be provided at a substantially middle position of the main body 221 along the axis direction of the bore 223. More descriptions for the channel may be found elsewhere in the present disclosure (e.g., FIGS. 5 and 6 and the descriptions thereof).

In some embodiments, the radiation source of the treatment head 212 may be disposed outside the main body 221 of the MRI device 220. For example, the treatment head 212 may be supported by the gantry 211 of the radiotherapy device 210. The radiation source of the treatment head 212 may be separated from the main body 221 and may rotate around the main body 221. In some embodiments, the radiation source of the treatment head 212 may be moved into the channel 222 (or a groove) when the radiotherapy device 210 is in a working period or in a non-running period via the movement of the gantry 211.

In some embodiments, the medical device 200 may include a couch 230. The couch 230 may be configured to support and/or transfer the at least one part of the subject (for example, a region in the bore 223 of the MRI device 220). The couch 230 may include a table top 231 and a supporting assembly 232. The supporting assembly 232 may support the table top 231. The couch 230 may move in any direction. For example, a longitudinal direction (i.e., along a long axis of table top 231 in the plane of the table top 231 at its retracted configuration), a lateral direction (i.e., along a short axis of the table top 231 in the plane of the table top 231 at its retracted configuration), or a direction oblique to the longitudinal direction and/or the lateral direction. The movement of the couch 230 may be driven manually or by, for example, a motor. In some embodiments, the couch 230 may be moved using a moveable device (e.g., a trolley or wheels) mounted on the couch 230.

In some embodiments, the MRI device 220 may further include a processor and a temperature sensor (not shown in FIG. 2). The temperature sensor may be configured to detect a temperature of at least one of the one or more heat conductors or the superconducting magnets and the processor may be configured to control an operation of the one or more refrigerators according to the temperature of at least one of the heat conductors or the superconducting magnet. For example, the temperature sensor may keep detecting the temperature of the heat conductors or the superconducting magnets when the MRI device 220 is performing imaging. As another example, the processor may guide the one or more refrigerators to refrigerate the one or more superconducting magnets according to the temperature.

It should be noted that the above description of the medical device 200 is merely provided for the purposes of illustration, and not intended to limit the scope of the present disclosure. For persons having ordinary skills in the art, multiple variations and modifications may be made under the teachings of the present disclosure. For example, the arrangement of the assemblies and/or functions of the medical device 200 may be varied or changed according to specific implementation scenarios.

Figure 5:
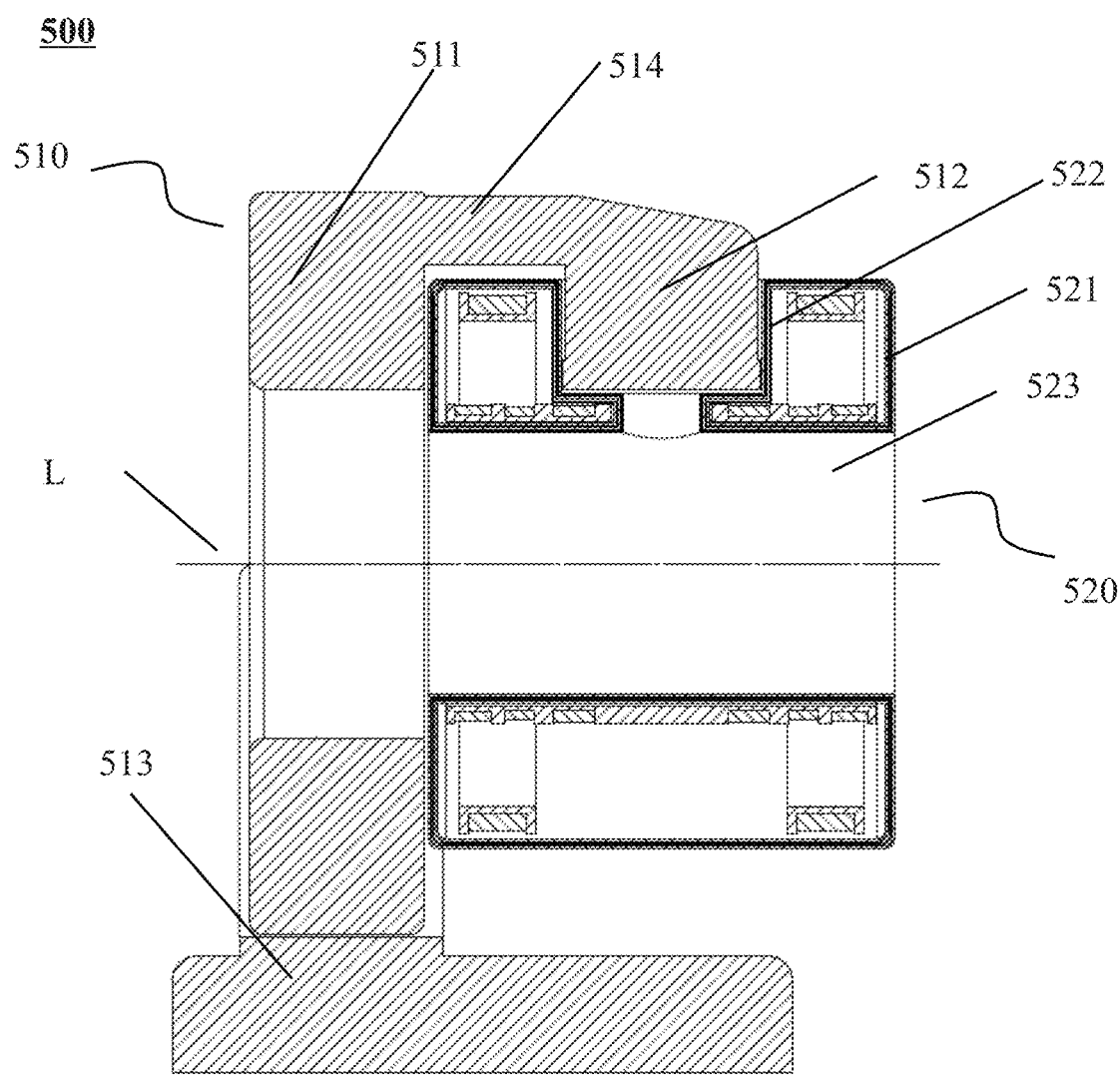
FIG. 5 is a cross-sectional view illustrating an exemplary medical device according to some embodiments of the present disclosure.

FIG. 5 is a schematic diagram illustrating a sectional view of an exemplary medical device according to some embodiments of the present disclosure. The sectional view of at least a portion of the medical device 500 as shown in FIG. 5 may be in a plane parallel to an axis of the medical device 500 denoted by line L. In some embodiments, the medical device 500 may be an exemplary embodiment of the medical device 110 and/or the medical device 200. In some embodiments, the medical device 500 may include a multi-modality device. For example, the medical device 500 may include a radiotherapy device 510 and an MRI device 520. The following descriptions are provided regarding the multi-modality device including the MRI device and the radiotherapy device unless otherwise stated. It should be noted that the descriptions of the MRI device and the radiotherapy device in the present disclosure are merely provided for illustration, and not intended to limit the scope of the present disclosure.

In some embodiments, the radiotherapy device 510 may include a gantry 511, a treatment head 512, a base 513, and a treatment arm 514. The treatment head 512 may be mounted on the gantry 511 via the treatment arm 514. The gantry 511 may be supported by the base 513. In some embodiments, the gantry 511 may rotate around the axis L of the medical device 500. The treatment head 512 and the treatment arm 514 may rotate along with the rotation of the gantry 511. In some embodiments, the gantry 511 may move along the vertical direction of the medical device 500. The treatment head 512 and the treatment arm 514 may move in the vertical direction along with the movement of the gantry 511.

In some embodiments, the MRI device 520 may include a main body 521 and a bore 523 configured to accommodate a subject. The MRI device 520 may include one or more superconducting magnets configured to generate a magnetic field in the bore 523. The direction of the magnetic field in the bore 523 may be parallel to the axis L of the medical device 500 that is the long axis of the bore 523. In some embodiments, the main body 521 may include multiple layers. For example, the main body 521 may include an inner vessel and an outer vessel. The inner vessel may include a cavity configured to accommodate the superconducting magnets. The outer vessel may include a vacuum container. The outer vessel may encompass the inner vessel. As another example, the main body 521 may include a heat exchange plate and/or one or more thermal shielding layers, etc.

In some embodiments, the main body 521 may include a channel 522 on a shell of the main body 521 along a direction substantially perpendicular to the direction of the magnetic field or the direction of the axis L of the medical device 500 (also referred to as an axial direction). For example, the outer vessel may be configured with a first through hole and the inner vessel may be configured with a second through hole. A diameter of the first through hole may exceed or equal to a diameter of the second through hole and the channel 522 may be formed by the first through hole and the second through hole. As another example, the shell of the main body 521 may include an inner wall and an outer wall. The outer wall may be configured with a first through hole and the inner wall may be configured with a second through hole. A diameter of the first through hole may exceed or equal to a diameter of the second through hole and the channel 522 may be formed by the first through hole and the second through hole. The inner wall and/or the inner vessel may be closer to the bore 523 than the outer wall and/or the outer vessel, respectively. The bore 523 may be formed by the inner wall or the inner vessel of the main body 521.

In some embodiments, at least a portion of the radiation source of the treatment head 512 may be disposed in the channel 522, and the radiation beams generated by the radiation source may pass through the channel 522 to the bore 523. In some embodiments, at least a portion of the radiation source of the treatment head 512 may be located in the bore 523. For example, at least a portion of the radiation source of the treatment head 512 may be out of the channel 522 such that a distance between the radiation source of the treatment head 512 may be closer to the subject in the bore 523. More descriptions for the channel 522 may be found elsewhere in the present disclosure (e.g., FIG. 6 and relevant descriptions thereof).

In some embodiments, the radiotherapy device 510 may be arranged such that the isocenter of the radiotherapy device may be coincide with the center point of the bore 523. As used herein, the isocenter of the radiotherapy device 510 may refer to an intersection of a rotation axis of the gantry 511 of the radiotherapy device 510 and a rotation axis of the radiation source (or the rotation axis of a collimator) of the radiotherapy device 510. More descriptions for the isocenter of the radiotherapy device 510 may be found in FIG. 10 and the descriptions thereof. In some embodiments, by setting the at least one portion of the treatment head 512 in the channel 522, the distance between the treatment head 512 and a center point of the bore 523 may be reduced, which may improve an efficiency of the radiotherapy device 510 for radiotherapy treatment. In some embodiments, a depth of the channel 522 may be no less than 40 centimeters, or no less than 50 centimeters, or no less than 60 centimeters, etc. In some embodiments, the distance between the treatment head 512 and the center point of the bore 523 (or the isocenter of the radiotherapy device 510) may be in a range of 40-50 centimeters. In some embodiments, the distance between the treatment head 512 and the center point of the bore 523 (or the isocenter of the radiotherapy device 510) may be in a range of 40-60 centimeters. In some embodiments, the distance between the treatment head 512 and the center point of the bore 523 (or the isocenter of the radiotherapy device 510) may be in a range of 30-50 centimeters. As used herein, the distance between the treatment head 512 and the center point of the bore 523 refers to a distance between the bottom of the treatment head 512 that is close to the bore 523 and the center point of the bore 523.

In some embodiments, the treatment head 512 may be moveable in the channel 522 to adjust the distance between the treatment head 512 and the center point of the bore 523 (or the isocenter of the radiotherapy device 510). For example, the distance between the treatment head 512 and the center point of the bore 523 (or the isocenter of the radiotherapy device 510) may be reduced by moving the treatment head 512 toward the bore 523, therefore improving the treatment efficiency of the treatment head 512.

In some embodiments, the medical device 500 may further include a processor (not shown in FIG. 5). The processor may be configured to control an operation of components in the medical device 500. For example, the processor may be configured to control the treatment head 512 and the main body 521 of the MRI device 520 to rotate simultaneously. As another example, the processor may be configured to control the treatment head 512 to perform radiotherapy, and control the MRI device 520 to perform image acquisition. Under the control of the processor, the MRI device 520 may obtain images while the radiotherapy device 510 is performing radiotherapy treatment. In some embodiments, the processor may guide the treatment head 512 to perform radiotherapy according to the images obtained by the MRI device 520. For example, the processor may control the treatment parameters of the radiotherapy device 510 according to the image data collected by the MRI device 520. The treatment parameters may include radiation dose, the rotation angle of the treatment head 512, or the like.

It should be noted that the above description of the medical device 500 is merely provided for the purposes of illustration, and not intended to limit the scope of the present disclosure. For persons having ordinary skills in the art, multiple variations and modifications may be made under the teachings of the present disclosure. For example, the arrangement of the assemblies and/or functions of the medical device 500 may be varied or changed according to specific implementation scenarios. As another example, the MRI device 520 may not include the channel 522 and the radiation source of the treatment head 512 may be located outside the main body 521 of the MRI device 500.

Figure 6:
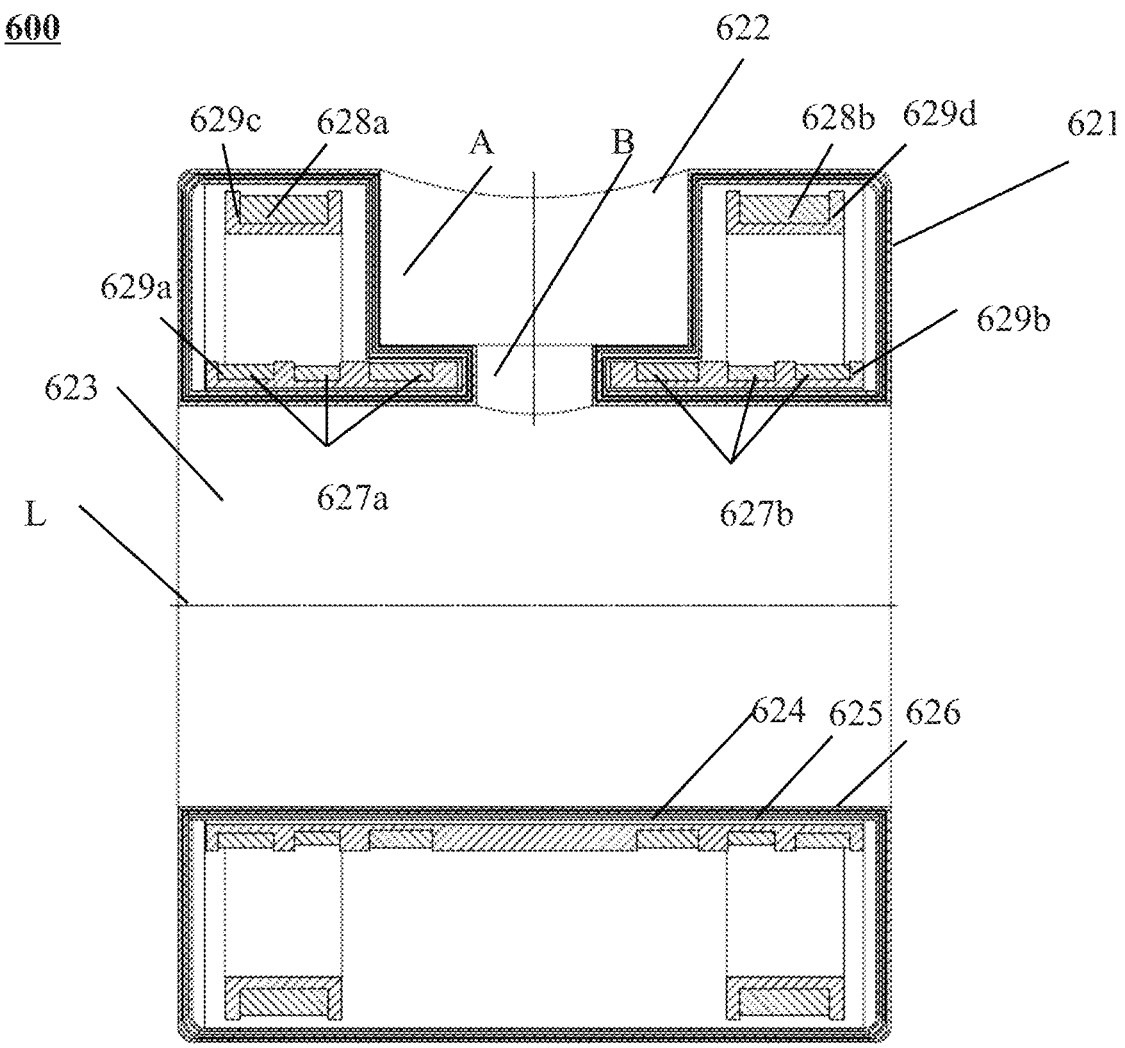
FIG. 6 is a schematic diagram illustrating a sectional view of the MRI device in a medical device according to some embodiments of the present disclosure.

FIG. 6 is a schematic diagram illustrating a sectional view of the MRI device in a medical device according to some embodiments of the present disclosure. In some embodiments, the MRI device 600 may be an exemplary embodiment of the MRI device in the medical device 110, the medical device 200, and/or the medical device 500. For example, the sectional view of at least a portion of the medical device 600 as shown in FIG. 6 may be in a plane parallel to the axis L of the medical device 500.

The MRI device 600 may include a main body 621 and a bore 623 configured to accommodate a subject. The MRI device 600 may include a superconducting magnet that is located in the main body 621. The superconducting magnet may include multiple superconducting coils. For example, the superconducting magnet may include multiple main coils and multiple shielding coils. The main coils may generate a magnetic field in the bore 623 (or inside the main coil) when the main coils are filled with a current. The direction of the magnetic field in the bore 623 or inside the main coils may be perpendicular to the direction of the current in the main coils. As shown in FIG. 6, the direction of the magnetic field in the bore 623 may be parallel with the axis L of the MRI device 600. The main coils may also generate a fringing magnetic field outside the main coils when the main coils are filled with a current, which may affect electronic components and/or the magnetic field in the bore 623 of the MRI device 600. The shielding coils may be configured to eliminate or decrease the intensity of the fringing magnetic field. For example, the shielding coils may be filled with a current with a direction that is opposite to the direction of the current in the main coils, and a magnetic field generated by the shielding coils may have an opposite direction with the fringing magnetic field generated by the main coils, so that the fringing magnetic field generated by the main coils may be canceled out by the magnetic field generated by the shielding coils.

In some embodiments, a first space may be formed between the shielding coils of the superconducting magnet such that at least a portion of a radiotherapy device (e.g., a treatment head) may be located in the first space. In some embodiments, the shielding coils may be connected by one or more superconducting connections (not shown in FIG. 6). In some embodiments, a second space may be formed between the main coils of the superconducting magnet such that radiation beams generated by the radiotherapy device may transmit to the bore 623 through the second space and not irradiate the main coils. The main coils may be connected by one or more superconducting connections (not shown in FIG. 6). The radiotherapy device may be designed to prevent the radiation beams generated by the radiotherapy device irradiating the one or more superconducting connections.

In some embodiments, the shell of the main body 621 of the MRI device 600 may include an inner wall and an outer wall. In some embodiments, the outer wall may be configured with a first through hole A and the inner wall may be configured with a second through hole B. A channel 622 may be formed by the first through hole and the second through hole. In some embodiments, a diameter of the first through hole A may exceed a diameter of the second through hole B. In some embodiments, the channel 622 may include a first portion corresponding to the first through hole A and a second portion corresponding to the second through hole B. In some embodiments, the treatment head of a radiotherapy device may be disposed in the channel 622 (e.g., the first portion of the channel 622) on the MRI device 600 for emitting a radiation beam to the bore 623 of the MRI device 600. The treatment head may emit a radiation beam to the bore 623 of the MRI device 600 through the second through hole B. The radiation beams may pass through the bore 623 without irradiating the shielding coils and/or the main coil, which avoids an attenuation of the energy of radiation beams.

As described in FIG. 6, the MRI device 600 may include a first main coil 627a and a second main coil 627b, a first shielding coil 628a, and a second shielding coil 628b. In some embodiments, the first main coil 627a and the second main coil 627b may be symmetrically distributed at both sides of the main body 621, and the first shielding coil 628a and the second shielding coil 628b may be symmetrically distributed at both sides of the main body 621. In some embodiments, the first main coil 627a and the second main coil 627b may be electrically connected through, for example, one or more superconducting connections (also referred to as first superconducting connections). In some embodiments, the first shielding coil 628a and the second shielding coil 628b may be electrically connected through, for example, one or more superconducting connections (also referred to as second superconducting connections).

In some embodiments, the main coils 627a and 627b and/or the shielding coils 628a and 628b may be in a superconducting state at least under certain conditions (e.g., when the coils are maintained at a suitable temperature, e.g., approximately 4.2 K). When current passes through the first main coil 627a and the second main coil 627b, a magnetic field may be generated in the bore 623, and the direction of the magnetic field in the bore 623 may be substantially parallel to the axis L. The strength of the magnetic field generated by the first main coil 627a and the second main coil 627b may be related to the number of turns of the first main coil 627a and the second main coil 627b. The direction of current in the first main coil 627a may be the same as the current in the second main coil 627b. The direction of current in the first shielding coil 628a and the second shielding coil 628b may be opposite to the direction of current in the first main coil 627a and the second main coil 627b. The direction of the magnetic field generated by the first shielding coil 628a and the second shielding coil 628b may be opposite to the fringing magnetic field generated by the first main coil 627a and the second main coil 627b. In some embodiments, the inner diameters of the first shielding coil 628a and the second shielding coil 628b may be larger than the outer diameters of the first main coil 627a and second main coil 627b so as to be able to decrease or eliminate the fringing magnetic field generated by the first main coil 627a and the second main coil 627b. In some embodiments, the first main coil 627a and the second main coil 627b may be electrically connected. In some embodiments, the first shielding coil 628a and the second shielding coil 628b may be electrically connected.

In some embodiments, the first main coil 627a and the second main coil 627b may be wound on a first bobbin 629a and a second bobbin 629b, respectively. The first shielding coil 628a and the second shielding coil 628b may be wound on a third bobbin 629c and a fourth bobbin 629d, respectively.

In some embodiments, the MRI device 600 may include a cooling assembly that is configured to cool the superconducting magnet (e.g., one or more main coils and one or more shielding coils) without using a coolant (e.g., liquid helium) to guarantee the superconducting magnet stays in a superconducting state. The cooling assembly may include one or more refrigerators and one or more heat conductors thermally connecting the one or more refrigerators and the superconducting magnets. In some embodiments, one of the one or more main coils and one of the one or more shielding coils may be thermally connected by one of the one or more heat conductors, and the one of the one or more heat conductors may be thermally connected with one of the one or more refrigerators. For example, the first main coil 627a and the first shielding coil 628a may be thermally connected by one of the one or more heat conductors and the one of the one or more heat conductors may be thermally connected with one of the one or more refrigerators. In some embodiments, one of the one or more main coils may be thermally connected with one of the one or more refrigerators via one of the one or more heat conductors and one of the one or more shield coils may be thermally connected with one of the one or more refrigerators via another one of the one or more heat conductors. For example, the first main coil 627a may be thermally connected with a refrigerator via one of the one or more heat conductors, and the first shielding coil 628a may be thermally connected with the refrigerator via another one of the one or more heat conductors. The first main coil 627a may be not thermally connected with the first shielding coil 628a. More descriptions for the cooling assembly may be found elsewhere in the present disclosure (e.g., FIGS. 7-8 and the descriptions thereof).

In some embodiments, a refrigerator may provide refrigeration to the superconducting magnets and/or other parts of the MRI device 600. In some embodiments, the refrigerator may include a cold head, a compressor assembly, and a coolant that operates in the refrigerator. When the gaseous coolant compressed by the compressor assembly (also referred to as high-pressure coolant) enters the cold head, the high-pressure coolant may expand and absorb a lot of heat to form the low pressure coolant, such that cold energy may be generated in the cold head. The cold energy may be transmitted to the superconducting magnets and/or other parts of the MRI device 600 via the one or more heat conductors. Then the low-pressure coolant may return to the compressor assembly and continue to compress and cycle.

In some embodiments, the MRI device 600 may include one or more heat exchange plates (for example, a heat exchange plate 624), one or more thermal shielding layers (for example, a thermal shielding layer 625), and one or more vacuum layers (for example, a vacuum layer 626) arranged around the superconducting magnet successively along the direction perpendicular to the axial direction from the inside out of the MRI device 600. The one or more heat exchange plates (for example, the heat exchange plate 624) may exchange heat with the superconducting magnets. The one or more thermal shielding layers (for example, the thermal shielding layer 625) may be located between the vacuum layers (for example, the vacuum layer 626) and the one or more heat exchange plates (for example, the heat exchange plate 624). The one or more thermal shielding layers (for example, the thermal shielding layer 625) may be configured to prevent heat exchange between the vacuum layers (for example, the vacuum layer 626) and the one or more heat exchange plates (for example, the heat exchange plate 624). The one or more vacuum layers (for example, the vacuum layer 626) may prevent heat exchange between the outside of the one or more vacuum layers (for example, a vacuum layer 626) and the inside of the one or more vacuum layers.

The heat exchange plate 624 may include a heat exchanger formed by stacking a series of metal sheets. The metal sheets may be in a certain corrugated shape. A thin rectangular channel may be formed between the various plates, and the heat may be exchange through the plates. The heat exchange plate has the characteristics of high heat exchange efficiency, low heat loss, compact and lightweight structure, small footprint, long service life, etc. The heat transfer coefficient of the heat exchange plate 624 may be 3-5 times higher than that of a tube heat exchanger, the covering area of the heat exchange plate 624 may be one-third of that of the tube heat exchanger, and the heat recovery rate can be as high as 90%. The heat exchange plate may be used to transfer the heat on the thermal shielding layer of the superconducting magnets, so as to achieve desired uniformity and/or stability of the temperature of the first main coil 627a and the second main coil 627b.

In some embodiments, the heat exchange plate 624 may be used to absorb heat generated by the superconducting magnets so as to achieve the desired uniformity and/or stability of the temperature of the superconducting magnets of the MRI device 600 (e.g., the first main coil 627a and the second main coil 627b). For example, the desired uniformity degree of the temperature of the superconducting magnet of the MRI device 600 (e.g., the first main coil 627a and the second main coil 627b) may be denoted by a difference between the highest temperature and the lowest temperature in the coils, which may be lower than 20° C., 15° C., 10° C., 8° C., 5° C., 2° C. or 1° C., etc. As used in this application, the desired stability degree of the temperature of the superconducting magnet of the MRI device 600 (e.g., the main coils 627a and 627b) may be denoted by the rate or value of the temperature change of the superconducting magnet of the MRI device 600 (e.g., the main coils 627a and 627b) (for example, compared with the standard temperature suitable for normal operation of the main coils), that may be lower than a respective threshold. For example, the desired stability degree of the temperature of the superconducting magnet of the MRI device 600 (e.g., the main coils 627a and 627b) may be that a temperature change rate in the coils is lower than 20° C./min, 15° C./min, 10° C./min, 8° C./min, 5° C./min, 2° C./min or 1° C./min etc. As another example, the desired stability degree of the temperature of the superconducting magnet of the MRI device 600 (e.g., the main coils 627a and 627b) may be that a temperature change value (for example, the deviation from the standard temperature) in any part of the superconducting magnet of the MRI device 600 is lower than 20° C., 15° C., 10° C., 8° C., 5° C., 2° C., 1° C., etc. As another example, the desired stability degree of the temperature of the superconducting magnet of the MRI device 600 (e.g., the first main coil 627a and the second main coil 627b) may be that a temperature change rate and a temperature change value of the first main coil 627a and the second main coil 627b (for example, compared with the standard temperature applicable to the normal operation of the main coil) are lower than the respective threshold value.

In some embodiments, the vacuum layer 626 may encompass the heat exchange plate 624 and the thermal shielding layer 625 may be located between the heat exchange plate 624 and the vacuum layer 626. The vacuum layer 626 may integrate different parts of the vacuum layer. The transfer of heat from the bore 623 or the outside of the vacuum layer to the main coils and/or the shielding coils of the MRI device 600 can be blocked, so that the temperature of the superconducting magnet of the MRI device 600 (e.g., the first main coil 627a and the second main coil 627b) can reach an ideal uniformity and/or stability.

In some embodiments, the one or more heat exchange plates (for example, the heat exchange plate 624), the one or more thermal shielding layers (for example, a thermal shielding layer 625), and one or more vacuum layers (for example, the vacuum layer 626) may be cooled by one of the one or more one or more refrigerators of the cooling assembly after absorbing heat from the superconducting magnets.

It should be noted that the above description of the MRI device 600 is merely provided for the purposes of illustration, and not intended to limit the scope of the present disclosure. For persons having ordinary skills in the art, multiple variations and modifications may be made under the teachings of the present disclosure. For example, the arrangement of the assemblies and/or functions of the MRI device 600 may be varied or changed according to specific implementation scenarios. As another example, the MRI device 600 may not include the channel 622 and the radiation source of the treatment head of a radiotherapy device may be located outside the main body 621 of the MRI device 600.

Figure 7:
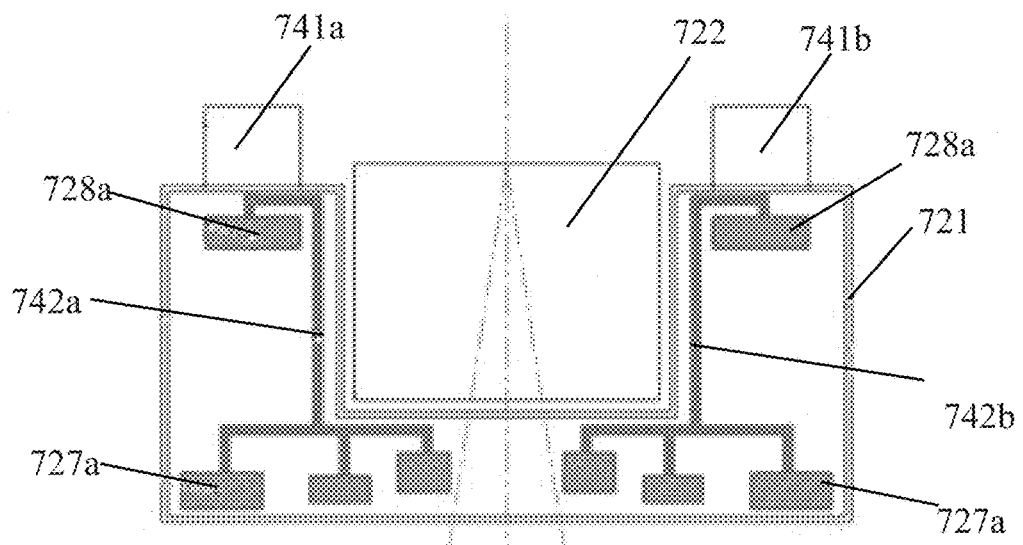
FIG. 7 is a schematic diagram illustrating a sectional view of a portion of an MRI device in a medical device according to some embodiments of the present disclosure.

FIG. 7 is a schematic diagram illustrating a sectional view of a portion of an MRI device in a medical device according to some embodiments of the present disclosure. In some embodiments, the MRI device 700 as described in FIG. 7 may be an exemplary embodiment of the MRI device in the medical device 110, the medical device 200, and/or the medical device 500. For example, the sectional view of at least a portion of the MRI device 700 as shown in FIG. 7 may be in a plane parallel to the axis L (also referred to as axial direction) of the medical device 500.

In some embodiments, the MRI device 700 may be the same as or similar to the MRI device 600 as described in FIG. 6. For example, the MRI device 700 may include a main body 721 and a bore configured to accommodate a subject. The MRI device 700 may include a superconducting magnet that is located in the main body. The superconducting magnet may include multiple superconducting coils. As shown in FIG. 7, the superconducting magnet may include a first main coil 727a, a second main coil 727b, a first shielding coil 728a, and a second shielding coil 728b. The first main coil 727*a* and second main coil 727*b* may be connected via one or more first superconducting connections (not shown). The first shielding coil 728*a* and the second shielding coil 728*b* may be electrically connected via one or more second superconducting connections (not shown). As another example, the MRI device 700 may include a heat exchange plate, a thermal shielding layer, and a vacuum layer arranged around the superconducting magnet successively along the direction perpendicular to the axial direction. As still another example, the main body 721 of the MRI device 700 may be provided with a channel 722 configured to accommodate at least a portion of a radiotherapy device. In some embodiments, the shell of the main body 721 of the MRI device 700 may include an inner wall and an outer wall. The outer wall may be configured with a first through hole and the inner wall may be configured with a second through hole. The channel 722 may be formed by the first through hole and the second through hole. In some embodiments, the diameter of the first through hole may equal a diameter of the second through hole. In some embodiments, the main body 721 of the MRI device 700 may be provided with a groove configured to accommodate at least a portion of a radiotherapy device. For example, the shell of the main body 721 of the MRI device 700 may include an inner wall and an outer wall. The outer wall may be provided with the groove configured to accommodate at least a portion of a radiotherapy device.

As shown in FIG. 7, a count of the one or more refrigerators may be equal to 2. The one or more refrigerators may include a first refrigerator 741*a* and a second refrigerator 741*b*. A count of the heat conductors may be equal to 2. The heat conductors may include a first heat conductor 742*a* and a second heat conductor 742*b*. Each of the first refrigerator 741*a* and the second refrigerator 741*b* may thermally connect one of the one or main coils and one of the one or more shielding coils through one of the one or more heat conductor located at a same side of the two sides of the channel. For example, the first main coil 727*a* and the first shielding coil 728*a* may be thermally connected via the first heat conductor 742*a*. The first heat conductor 742*a* may be thermally connected with the first refrigerator 741*a*. The second main coil 727*b* and the second shielding coil 728*b* may be thermally connected via the second heat conductor 742*b*. The second heat conductor 742*b* may be thermally connected with the second refrigerator 741*b*. As another example, the first main coil 727*a* may be directly connected with the first refrigerator 741*a* via a heat conductor; and the first shielding coil 728*a* may be directly connected with the first refrigerator 741*a* via a heat conductor. The second main coil 727*b* may be directly connected with the second refrigerator 741*b* via a heat conductor; and the second shielding coil 728*b* may be directly connected with the second refrigerator 741*b* via a heat conductor.

In some embodiments, the main coils may work normally under a low temperature (e.g., approximately 4.2 K). The low temperature may be guaranteed by the one or more refrigerators and the heat conductors. In some embodiments, a heat conductor may be configured to perform a heat exchange between the superconducting magnet (e.g., the main coils and the shielding coils) and one of the one or more refrigerators that is thermally connected with the head conductor. For example, the heat conductor may transfer heat generated by the superconducting magnet (e.g., the main coils and the shielding coils) to one of the one or more refrigerators that are thermally connected with the head conductor. A refrigerator may include a cold head. The cold head may provide refrigeration to the superconducting magnet (e.g., the main coils and the shielding coils) via a heat conductor that is thermally connected with the refrigerator to maintain the temperature of the superconducting magnet, e.g., the main coils and the shielding coils (e.g., approximately 4.2 K). In some embodiments, a refrigerator may thermally connect one or more layers of the shell of the main body 721, e.g., the heat exchange plate, the thermal shielding layer. The refrigerator may provide refrigeration to the one or more layers of the shell of the main body 721, e.g., the heat exchange plate, the thermal shielding layer to cool the one or more layers of the shell of the main body 721 when the one or more layers of the shell of the main body 721 absorb heat from the superconducting magnet, e.g., the main coils and the shielding coils.

In some embodiments, the one or more heat conductors may be made of a metal material. The metal material may include one or more types of metals, an alloy material, etc. Specifically, a thermal conductivity of the metal material may exceed a certain threshold. In some embodiments, the threshold may be 200 W/mK. That is, the metal material with the thermal conductivity exceeding 200 W/mK may be used as heat conductors. For example, the metal material may include gold, silver, copper, aluminum, etc. In some embodiments, the threshold may be equal to 250 W/mK, or 300 W/mK, or 400 W/mK, etc.

It should be noted that the above description of the MRI device 700 is merely provided for the purposes of illustration, and not intended to limit the scope of the present disclosure. For persons having ordinary skills in the art, multiple variations and modifications may be made under the teachings of the present disclosure. For example, the arrangement of the assemblies and/or functions of the MRI device 700 may be varied or changed according to specific implementation scenarios. For example, the cooling assembly may include one single refrigerator. As another example, the superconducting magnet may include more main coils except for the first main coil 727*a* and the second main coil 727*b* and/or more shielding coils except for the first shielding coil 728*a* and the second shielding coil 728*b*.

Figure 8:
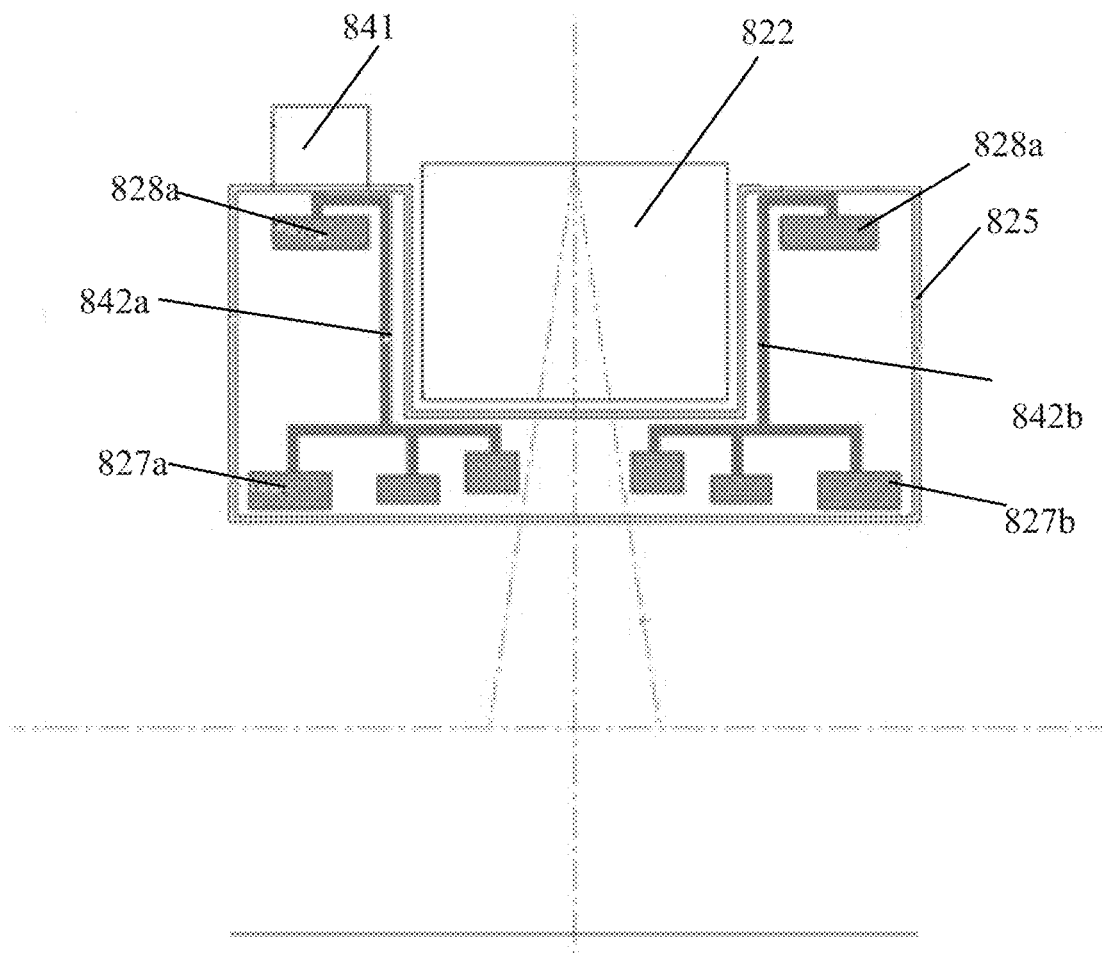
FIG. 8 is another schematic diagram illustrating a sectional view of a portion of an MRI device according to some embodiments of the present disclosure.

FIG. 8 is another schematic diagram illustrating a sectional view of a portion of an MRI device according to some embodiments of the present disclosure. In some embodiments, the MRI device 800 as described in FIG. 8 may be an exemplary embodiment of the MRI device in the medical device 110, the medical device 200, and/or the medical device 500. For example, the sectional view of at least a portion of the MRI device 800 as shown in FIG. 8 may be in a plane parallel to the axis L (also referred to as axial direction) of the medical device 500.

In some embodiments, the MRI device 800 may be the same as or similar to the MRI device 600 as described in FIG. 6. For example, the MRI device 800 may include a main body and a bore configured to accommodate a subject. The MRI device 800 may include a superconducting magnet that is located in the main body. The superconducting magnet may include multiple superconducting coils. For example, the superconducting magnet may include a first main coil 827*a*, a second main coil 827*b*, a first shielding coil 828*a*, and a second shielding coil 828*b*. The first main coil 827*a* and the second main coil 827*b* may be connected via one or more first superconducting connections (not shown). The first shielding coil 828*a* and the second shielding coil 828*b* may be connected via one or more second superconducting connections (not shown). In some embodiments, at least one of the first main coil 827*a* or the second main coil 827*b* may be connected with at least one of the first shielding coil 828*a* or the second shielding coil 828*b* via one or more third superconducting connections (not shown). More descriptions for the superconducting connections may be found elsewhere in the present disclosure. As another example, the MRI device 800 may include a heat exchange plate, a thermal shielding layer 825 and a vacuum layer 826 arranged around the superconducting magnet successively along the direction perpendicular to the axial direction. As still another example, the main body of the MRI device 800 may be provided with a channel 822 configured to accommodate at least a portion of a radiotherapy device.

As shown in FIG. 8, a count of the refrigerators may be equal to 1. The refrigerator may include a single refrigerator 841. A count of the heat conductors may be equal to 2. The heat conductors may include a first heat conductor 842*a* and a second heat conductor 842*b*. The heat conductors 842*a* and 842*b* may be used to thermally connect the refrigerator 841 with the superconducting magnet.

In some embodiments, the single refrigerator may thermally connect with one of the one or more shielding coils through one of the one or more heat conductors (i.e., the first heat conductor 842*a* and the second heat conductor 842*b*). For example, the refrigerator 841 may be thermally connected with the first shielding coil 828*a* via the first heat conductor 842*a*. The first heat conductor 842*a* may be thermally connected with the refrigerator 841. The first shielding coil 828*a* may be thermally connected with the first main coil 827*a* via the first heat conductor 842*a*. The second main coil 827*b* and the second shielding coil 828*b* may be thermally connected via the second heat conductor 842*b*. The first main coil 827*a* and the second main coil 827*b* may be physically connected by the first superconducting connections.

As another example, the first main coil 827*a* may be thermally connected with the refrigerator 841 via the first heat conductor 842*a*; and the first shielding coil 828*a* may be thermally connected with the refrigerator 841 via the first heat conductor 842*a*. The first main coil 827*a* and the first shielding coil 828*a* may be not thermally connected.

In some embodiments, a heat conductor (e.g., the first heat conductor 842*a* or the second heat conductor 842*b*) may be configured to perform heat exchange between the superconducting magnet (e.g., the main coils and the shielding coils) and the refrigerator 841 that is thermally connected with the head conductor. For example, the first heat conductor 842*a* may transfer heat generated by the superconducting magnet (e.g., the main coils and the shielding coils) to the refrigerator 841. In some embodiments, the refrigerator 841 may be a Gifford-Mcmahon refrigerator. The cold head may provide refrigeration to the superconducting magnet (e.g., the main coils and the shielding coils) via the heat conductors (e.g., the first heat conductor 842*a* and the second heat conductor 842*b*) that is thermally connected with the refrigerator 841 to maintain the temperature of the superconducting magnet, e.g., the main coils and the shielding coils (e.g., approximately 4.2 K). For example, the cold head may provide refrigeration to the first main coil 827*a* and the first shielding coil 828*a* via the first heat conductor 842*a*. The refrigeration provided to the first main coil 827*a* may be transferred to the second main coil 827*b* through the superconducting connections between the first main coil 827*a* and the second main coil 827*b*. The refrigeration provided to the first shielding coil 828*a* may be transferred to the second shielding coil 828*b* through the superconducting connections between the first shielding coil 828*a* and the second shielding coil 828*b*. The refrigeration provided to the second shielding coil 828*b* may be transferred to the second main coil 827*b* through the second heat conductor 842*b* between the second shielding coil 828*b* and the second main coil 827*a*.

In some embodiments, the refrigerator 841 may thermally connect one or more layers of the shell of the main body, e.g., the heat exchange plate, the thermal shielding layer. The refrigerator 841 may provide refrigeration to the one or more layers of the shell of the main body, e.g., the heat exchange plate, the thermal shielding layer to cool the one or more layers of the shell of the main body when the one or more layers of the shell of the main body absorb heat from the superconducting magnet, e.g., the main coils and the shielding coils.

In some embodiments, the one or more heat conductors may be made of a metal material. The metal material may include one or more metals, an alloy material, etc. Specifically, a thermal conductivity of the metal material exceeds a certain threshold. For example, the metal material may include gold, silver, copper, etc. More descriptions for the heat conductors may be found elsewhere in the present disclosure. In some embodiments, the heat conductors may be arranged in a non-radiation irradiation area to avoid the influence of radiation irradiation on the conductive effect.

It should be noted that the above description of the MRI device 800 is merely provided for the purposes of illustration, and not intended to limit the scope of the present disclosure. For persons having ordinary skills in the art, multiple variations and modifications may be made under the teachings of the present disclosure. For example, the arrangement of the assemblies and/or functions of the MRI device 800 may be varied or changed according to specific implementation scenarios. As another example, the superconducting magnet may include more main coils except for the first main coil 827*a* and the second main coil 827*b* and/or more shielding coils except for the first shielding coil 828*a* and the second shielding coil 828*b*.

Figure 9:
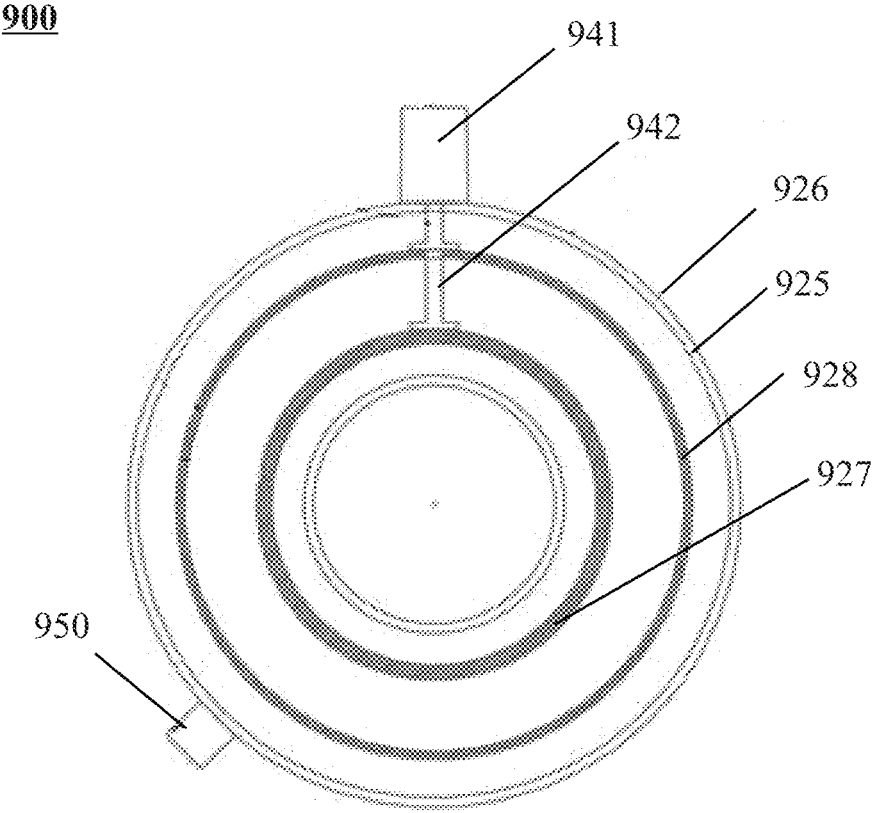
FIG. 9 is a schematic diagram illustrating a sectional view of an MRI device according to some embodiments of the present disclosure.

FIG. 9 is a schematic diagram illustrating a sectional view of an MRI device according to some embodiments of the present disclosure. In some embodiments, the MRI device 900 as described in FIG. 9 may be an exemplary embodiment of the MRI device in the medical device 110, the medical device 200, and/or the medical device 500. For example, the sectional view of at least a portion of the MRI device 900 as shown in FIG. 9 may be in a plane perpendicular to the axis L (also referred to as axial direction) of the medical device 500.

In some embodiments, the MRI device 900 may be the same as or similar to the MRI device 600 as described in FIG. 6. For example, the MRI device 900 may include a main body and a bore configured to accommodate a subject. The MRI device 900 may include a superconducting magnet that is located in the main body. The superconducting magnet may include multiple superconducting coils. For example, the superconducting magnet may include one or more main coils 927 and one or more shielding coils 928. As another example, the MRI device 900 may include a heat exchange plate, a thermal shielding layer 925 and a vacuum layer 926 arranged around the superconducting magnet successively along the direction perpendicular to the axial direction. As still another example, the MRI device 900 may include a cooling assembly configured to cool the one or more superconducting magnets. The cooling assembly may include one or more refrigerators 941 and one or more heat conductors 942 physically connecting the one or more refrigerators 941 and the one or more superconducting magnets (e.g., the one or more main coils 927 and the one or more shielding coils 928).

Figure 10:
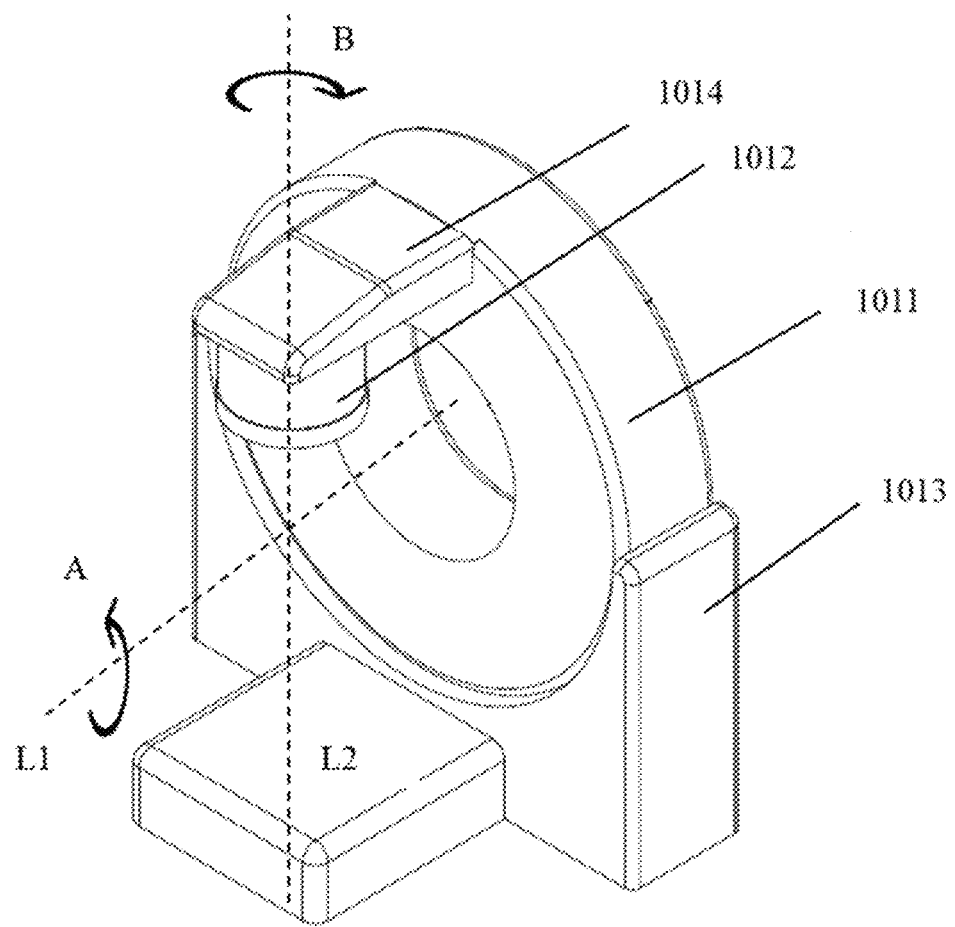
FIG. 10 is a schematic diagram illustrating an exemplary radiotherapy device in a medical device according to some embodiments of the present disclosure.

As shown in FIG. 10, the MRI device may include a vacuum port 950 for vacuuming the main body. In some embodiments, the vacuum port 950 may be mounted on the vacuum layer 926. The vacuum layer 926 may include a vacuum container. The vacuum port 950 may be configured to provide gas communication between the vacuum layer 926 and a source of negative pressure (e.g., a vacuum pump). For example, the pressure in the cavity of the vacuum layer 926 may be adjusted by the vacuum port 950 and the source of negative pressure (e.g., a vacuum pump). Further, the source of negative pressure (e.g., a vacuum pump) may render the cavity of the vacuum layer 926 via the vacuum port 950 to include space of vacuum or substantially of vacuum.

It should be noted that the above description of the MRI device 900 is merely provided for the purposes of illustration, and not intended to limit the scope of the present disclosure. For persons having ordinary skills in the art, multiple variations and modifications may be made under the teachings of the present disclosure. For example, the arrangement of the assemblies and/or functions of the MRI device 900 may be varied or changed according to specific implementation scenarios.

FIG. 10 is a schematic diagram illustrating an exemplary radiotherapy device in a medical device according to some embodiments of the present disclosure. In some embodiments, the radiotherapy device 1000 as described in FIG. 10 may be an exemplary embodiment of the radiotherapy device in the medical device 110, the medical device 200, and/or the medical device 500.

The radiotherapy device 1000 may include a gantry 1011, a treatment head 1012, a base 1013, and a treatment arm 1014. The treatment head 1012 may be mounted on the gantry 1011. The gantry 1011 may be supported by the base 1013. The treatment head 1012 may include a radiation source that is configured to emit a radiation beam.

In some embodiments, the gantry 1011 may rotate in a first direction denoted by arrow A. In other words, the gantry 1011 may rotate around the axis of the radiotherapy device 1000 denoted by a dotted line L1 (also referred to as a rotation axis of the gantry 1011). The rotation of the gantry 1011 may cause the rotation of the treatment arm 1014 and the treatment head 1012 around the axis of the radiotherapy device 1000. In some embodiments, the treatment head 1012 may rotate in a second direction denoted by arrow B. In other words, the treatment head 1012 may rotate around the axis of the radiotherapy device 1000 denoted by a dotted line L2 (also referred to as a rotation axis of the treatment head 1012 or the radiation source of the treatment heat 1012). The intersection between the rotation axis of the gantry 1011 and the rotation axis of the treatment head 1012 may be the isocenter of the radiotherapy device 1000.

In some embodiments, the treatment head 1012 may be embedded in a main body of an MRI device to form a multi-modality device. For example, the main body of the MRI device may be provided with a channel. The treatment head 1012 may be located in the channel. More descriptions for the radiotherapy device 1000 and the multi-modality device may be found elsewhere in the present disclosure. For example, FIG. 2 and relevant descriptions thereof.

It should be noted that the above description of the radiotherapy device 1000 is merely provided for the purposes of illustration, and not intended to limit the scope of the present disclosure. For persons having ordinary skills in the art, multiple variations and modifications may be made under the teachings of the present disclosure. For example, the arrangement of the assemblies and/or functions of the radiotherapy device 1000 may be varied or changed according to specific implementation scenarios.

Figure 11:
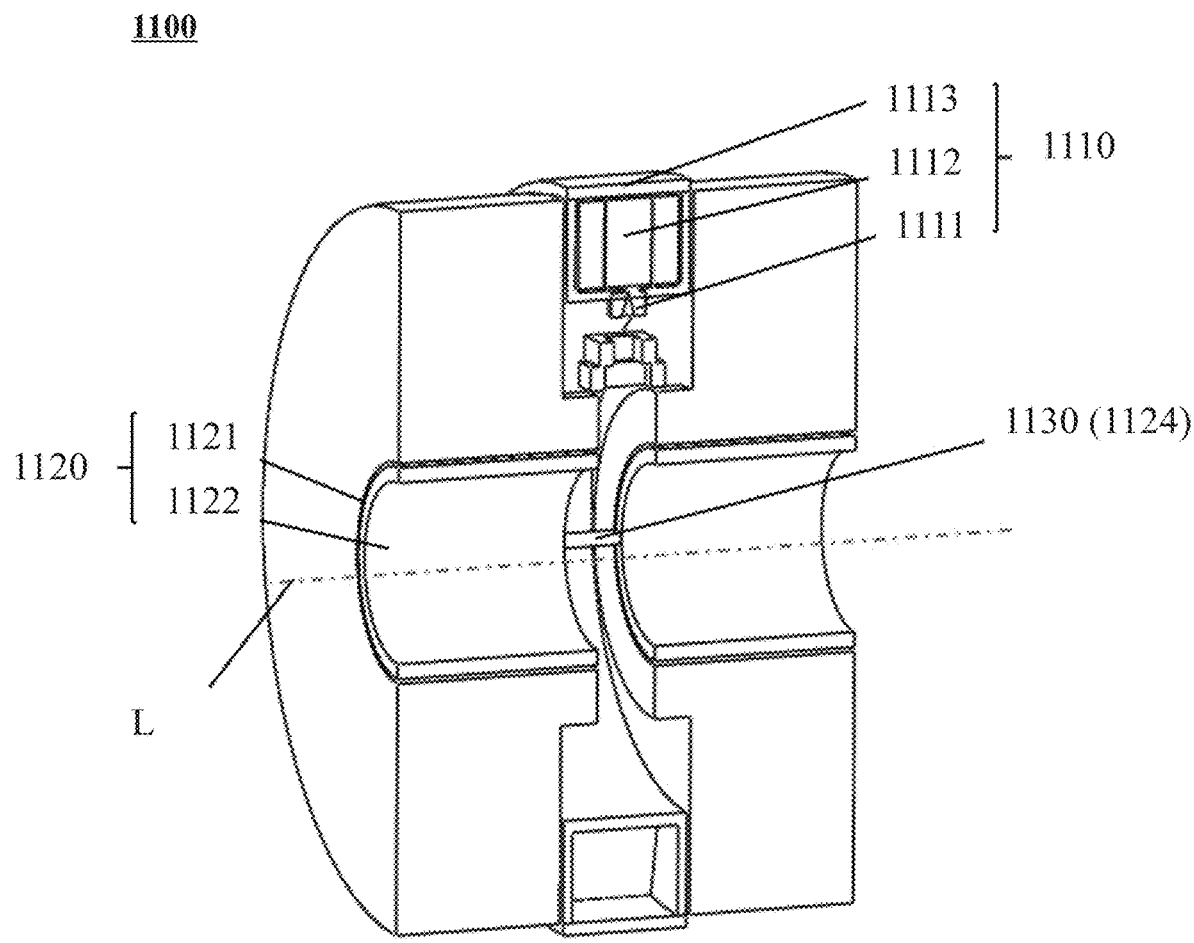
FIG. 11 is a schematic diagram illustrating an exemplary medical device according to some embodiments of the present disclosure.

FIG. 11 is a schematic diagram illustrating an exemplary medical device according to some embodiments of the present disclosure. In some embodiments, the medical device 1100 may be an exemplary embodiment of the medical device 110. In some embodiments, the medical device 1100 may include a multi-modality device. The following descriptions are provided regarding the multi-modality device including an MRI device and a radiotherapy device unless otherwise stated. It should be noted that the descriptions of the MRI device and the radiotherapy device in the present disclosure are merely provided for illustration, and not intended to limit the scope of the present disclosure.

The medical device 1100 may include a radiotherapy device 1110 and a magnetic resonance imaging device (MRI) 1120.

In some embodiments, the radiotherapy device 1110 may include a linear accelerator (LINAC) configured for irradiating at least a portion of a subject (such as tumors in the patient) by accelerating electrons, ions, or protons. The radiotherapy device 1110 may include a treatment head 1111, a treatment arm 1112, and a gantry 1113. The treatment head 1111 may be mounted on the gantry 1113 by the treatment arm 1112. In some embodiments, the radiotherapy device 1110 may also include a base (not shown). The gantry 1113 may be mounted on the base and supported by the base. The treatment head 1111 may be configured to emit a radiation beam. Specifically, the treatment head 1111 may include a radiation source configured to generate and emit radiation beams. In some embodiments, the radiation beams may include an X-ray beam, an electron beam, a gamma beam, a proton beam, or the like.

In some embodiments, the MRI device 1120 may include a main body 1121. As used herein, the main body 1121 refers to a shell for wrapping and/or supporting parts (e.g., a superconducting magnet, etc.) of the MRI device 1120. In some embodiments, the main body 1121 of the MRI device 1120 may include a bore 1122 configured to accommodate a subject. The subject may be accommodated in the bore for imaging and/or treatment. The treatment head 1112 may emit radiation rays toward the bore 1122 of the MRI device 1120 for radiotherapy treatment.

In some embodiments, the MRI device 1120 may include one or more superconducting magnets, one or more gradient coils, and one or more radio frequency (RF) coils that may be accommodated in the main body 1121. The one or more superconducting magnets may be configured to generate a magnetic field during MRI. In some embodiments, one of the one or more superconducting magnets may include a main coil and a shielding coil (not shown in FIG. 11). The MRI device 1120 may further include one or more superconducting connections 1124 each of which is configured to connect at least two of the one or more superconducting magnets. For example, the superconducting connections may be configured to connect two main coils of the one or more superconducting magnets. More descriptions for the main coils and shielding coils and superconducting connections may be found elsewhere in the present disclosure, see FIG. 14 and relevant descriptions.

In some embodiments, the MRI device 1120 may further include one or more protection components 1130 configured to absorb at least a portion of radiation beams when the radiation beams transmit toward the one or more superconducting connections 1124. In some embodiments, each of the one or more superconducting connections 1124 may be located in one of the one or more protection components 1130. In some embodiments, the protection components 1130 may include a material with a high attenuation coefficient. For example, the material may include lead, tungsten, etc.

In some embodiments, the main body 1121 of the MRI device 1120 may include two portions separated from each other. The one or more superconducting magnets may be accommodated in the two portions of the main body of the MRI device 1120, respectively. In some embodiments, the two portions of the main body 1121 of the MRI device 1120 may be integrated into a whole body. In some embodiments, space may be formed between the one or more superconducting magnets 1121. For example, the space may be formed between the two portions of the main body 1121 of the MRI device 1120. The superconducting connections 1124 and the protection components 1130 be located in the space. In some embodiments, at least a portion of the radiotherapy device 1110 may be located in the space. For example, the treatment head 1111 may be located and/or rotated in the space. The radiation beams generated by the treatment head 1111 may be emitted toward the bore 1122 through the space. In some embodiments, the main body 1121 may include a channel or a groove as described elsewhere in the present disclosure configured to accommodate the treatment head 1111 and/or the treatment arm 1112.

In some embodiments, the treatment head 1111 may rotate around a Z-axis of the MRI device 1120 denoted by dotted line L. The direction of the Z-axis of the MRI device 1120 denoted by dotted line L may be the same as the direction of the magnetic field provided by the one or more superconducting magnets. In other words, the treatment head 1111 may rotate around the axis L of the MRI device 1120 in a plane perpendicular to the axis L of the MRI device 1120 in the space. As another example, the treatment head 1111 may be located outside the main body 1121 and rotate around the axis L of the MRI device 1120.

In some embodiments, the MRI device 1120 may be fixed on a base same as the base of the radiotherapy device 1110. In some embodiments, the MRI device 1120 may be fixed on a base different from the base of the radiotherapy device 1110. In some embodiments, the treatment head 1111 and the main body of the MRI device 1120 may rotate separately. In some embodiments, the treatment head 1111 and the main body 1121 of the MRI device 1120 may rotate around a common axis simultaneously. In some embodiments, the MRI device 1120 may perform an imaging scan when the radiotherapy device 1110 performs radiotherapy treatment which improves the efficiency and reliability for diagnosis and treatment.

By arranging at least part of the superconducting connections 1124 in the protection components 1130 that has a shielding function for the radiation beams, it may effectively prevent the radiation beams from the treatment head 1111 of the radiotherapy device 1110 from irradiating the superconducting connections and causing the magnetic field on the MRI device to be quenched, thereby ensuring the normal operation of the MRI device. In some embodiments, the radiotherapy device 1110 and the MRI device 1120 may be used separately, sequentially, or simultaneously.

It should be noted that the above description of the medical device 200 is merely provided for the purposes of illustration, and not intended to limit the scope of the present disclosure. For persons having ordinary skills in the art, multiple variations and modifications may be made under the teachings of the present disclosure. For example, the arrangement of the assemblies and/or functions of the medical device 1100 may be varied or changed according to specific implementation scenarios. As another example, the treatment arm 1112 may not be located in the main body 1121.

Figure 12:
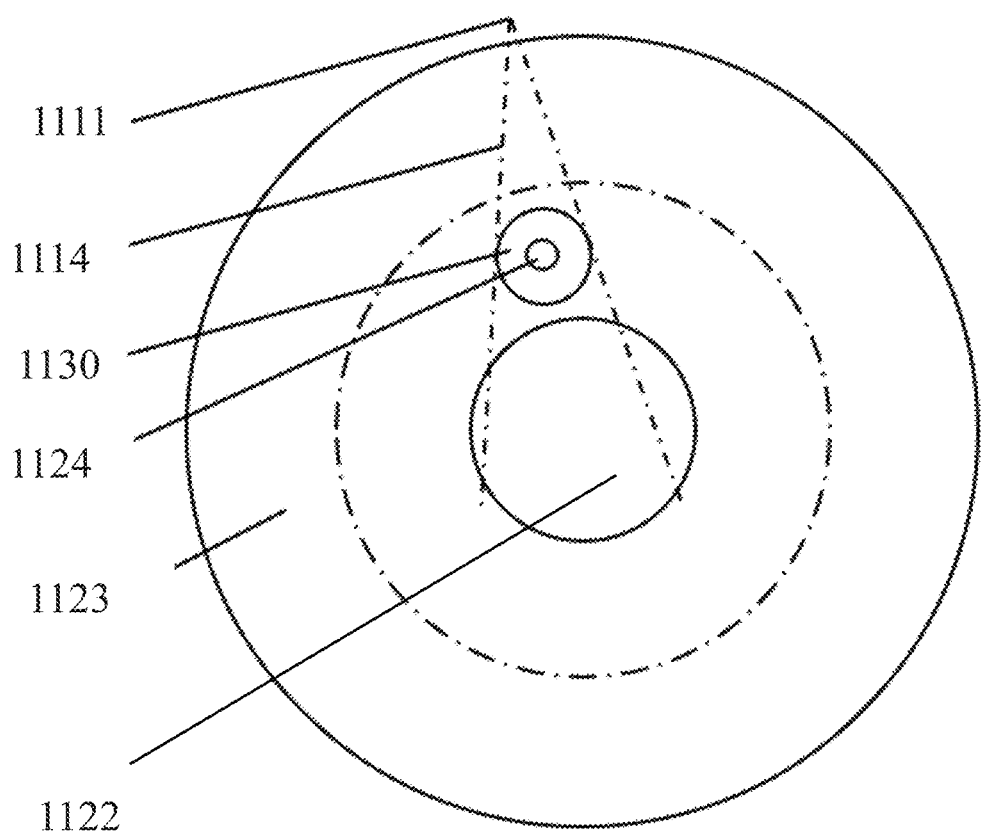
FIG. 12 is schematic diagram illustrating a sectional view of the medical device 1100 including an exemplary protection component according to some embodiments of the present disclosure.
Figure 13:
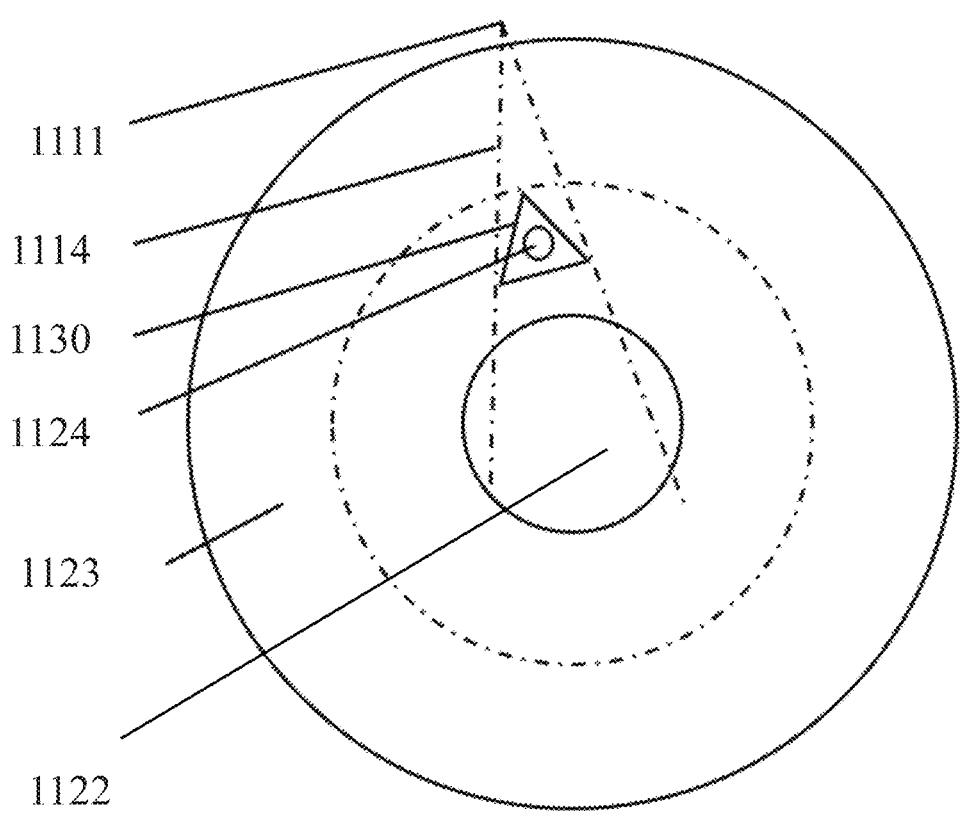
FIG. 13 is schematic diagram illustrating a sectional view of the medical device 1100 including another exemplary protection component according to some embodiments of the present disclosure.

FIG. 12 is schematic diagram illustrating a sectional view of the medical device 1100 including an exemplary protection component according to some embodiments of the present disclosure. FIG. 13 is schematic diagram illustrating a sectional view of the medical device 1100 including another exemplary protection component according to some embodiments of the present disclosure. FIG. 12 and FIG. 13 show the sectional views of the medical device 1100 in a plane perpendicular to the axis L of the MRI device 1120 as shown in FIG. 11.

In some embodiments, the MRI device 1120 may include a cryostat 1123 as shown in FIG. 12 and FIG. 13. The cryostat 1123 may include a coolant (e.g., liquid helium) configured to keep the superconducting magnets that are located in the cryostat 1123 under a low working temperature (e.g., approximately 4.2 K) so that the superconducting magnets accommodated in the cryostat 1123 may stay in the superconducting state. The cryostat 1123 may include multiple vessels to reduce heat exchange between the internal and external of the cryostat 1123. In some embodiments, the cryostat 1123 may include an inner vessel, an outer vessel encompassing the inner vessel, and a thermal shielding layer configured between the outer vessel and the inner vessel. The inner vessel may be configured to accommodate one or more superconducting magnets and a coolant (e.g., liquid helium). The inner vessel may also be referred to as a liquid helium container. The outer vessel may include a vacuum container. As shown in FIG. 12-13, the cryostat 1123 may have a closed ring shape.

The superconducting magnets may be electronically connected by the superconducting connections 1124 so that space may be formed between two connected superconducting magnets. Therefore, radiation beams 1114 emitted by the treatment head 1111 may transmit to the bore 1122 via passing through the space between two connected superconducting magnets 1121 to irradiate a subject located in the bore 1122. The superconducting connections 1124 may be made of a conductive material, such as copper, aluminum, etc.

In some embodiments, the radiation beams 1114 (e.g., X-rays) emitted from the treatment head 1111 may pass through the cryostat 1123, e.g., a shell of the liquid helium container, the thermal shielding layer and the shell of the vacuum container of the main body of the MRI device 1120, and the liquid helium inside. In addition, the one or more superconducting connections 1124 connecting at least two of the multiple superconducting magnets 1121 may be possible to be irradiated by the radiation beams in the rotation of the treatment head 1111 or the gantry 1113, which may cause the temperature of the superconducting connections 1124 raise and a quenching of the superconducting magnets. In some embodiments, the radiotherapy device 1110 may keep the radiation rays from irradiating the areas where the superconducting connections 1124 are located. For example, when the radiation field of the treatment head 1111 includes the areas in the rotation of the gantry 1113, the radiotherapy device 1110 may stop to generate radiation beams for irradiating the areas.

In some embodiments, the radiotherapy device 1110 may be designed to rotate around with the Z-axis L such that the radiation beams emitted by the treatment head 1111 do not irradiate the superconducting connections 1124. For example, when the gantry 1113 of the radiotherapy device 1110 rotates in an angle range, the radiation beams emitted by the treatment head 1111 may irradiate the superconducting connections 1124. Then a prohibited area may be determined to prevent the radiation beams emitted by the treatment head 1111 to irradiate the superconducting connections 1124 based on the locations of the superconducting connections 1124. The prohibited area may be defined by a rotation angle of the gantry 1113 and locations of the superconducting connections 1124. For example, if the locations of the superconducting connections 1124 are around 13 degrees of the rotation angle of the gantry 1113, the prohibited area may be defined by 9 degrees to 17 degrees of the rotation angle of the gantry 1113. In other words, the gantry 1113 may be prohibited to rotate 9 degrees to 17 degrees.

In some embodiments, the protection components 1130 may be applied in the MRI device 1120 which can effectively prevent the radiation beams (e.g., X-rays) from generating energy deposition on the superconducting connections 1123 when the radiation beams transmit toward the superconducting connections 1124.

In some embodiments, at least part of the superconducting connections 1124 may be located in the protection components 1130, respectively. For example, the superconducting connections 1124 located in a potential irradiation area of the radiation beams may be located in the protection component 1130. In some embodiments, the potential irradiation area refers to an area that the treatment head 1111 may irradiate. Since the MRI device 1120 and the radiotherapy device 1110 may work independently, the treatment head 1111 may rotate relative to the main body of the MRI device 1120 while the MRI device 1120 is immobilized. If the radiation beams emitted by the treatment head 1111 irradiates the superconducting connections 1124 (for example, the temperature of the superconducting connections 1124 are increased), it may cause the superconducting magnets 1121 of the MRI device 1120 to loss superconductivity, thereby causing the MRI device 1120 cannot work normally. The superconductivity loss of the superconducting magnet 1121 caused by the radiation beams irradiating the superconducting connections 1124 may be effectively solved according to setting the protection components 1130. The superconducting magnets, the superconducting connections 1124 for connecting the superconducting magnets, and the protection components 1130 may all be located in the cryostat 1123. When the radiation beams 1114 emitted by the treatment head 1111 transfers toward the superconducting connections 1124, at least a portion of the radiation beams 1114 may be absorbed by the protection components 1130, which decreases the energy of radiation beams deposited on the superconducting connections 1124, thereby decreasing the risk of loss of superconductivity of the superconducting connections 1124.

In some embodiments, the protection components 1130 may include a material with an attenuation coefficient exceeding a threshold. The threshold may be 3000/cm, 2000/cm, 1000/cm, etc. For example, the materials with an attenuation coefficient exceeding 2000/cm may have a high density, such as tungsten, lead, or the like. The higher the threshold is, the higher the attenuation coefficient, the better the radiation shielding effect of the materials may be.

In some embodiments, the protection components 1130 may include a material with a thermal conductivity less than a threshold. The threshold may be 2 W/m·K, 4 W/m·K, 8 W/m·K, 10 W/m·K, 20 W/m·K, etc. For example, the materials with a thermal conductivity less than 2 W/m. K may be materials with less thermal conductivity, heat preservation and heat insulation functions such as ceramics, thermal insulation cotton, polystyrene foam board, polyurethane foam, glass fiber cotton, etc. The threshold refers to a threshold relating to the thermal conductivity, the lower the threshold is, the worse the thermal conductivity of the material may be, and the better the heat preservation effect may be.

In some embodiments, at least one of the protection components 1130 may include multiple layers. For example, at least one of the protection components 1130 may include a radiation shielding layer and a thermal insulation layer. The radiation shielding layer may be made of materials with a high attenuation coefficient and a high density, such as tungsten, lead, or the like. The thermal insulation layer may be made of ceramics, a thermal insulation cotton, a polystyrene foam board, a polyurethane foam, a glass fiber cotton, or other thermal insulation materials.

In some embodiments, at least one of the protection components 1130 may include a tubular structure and one of the one or more superconducting connections 1124 may be arranged in the tubular structure. In some embodiments, at least one of the protection components 1130 may be a hollow cylindrical structure (as shown in FIG. 12). In some embodiments, at least one of the protection components 1130 may be a hollow triangular prism structure (as shown in FIG. 13). In some alternative embodiments, at least one of the protection components 1130 may be a quadrangular prism structure, a pentagonal prism structure, or the like. Since the protection components 1130 has the functions of shielding radiation beams, thermal insulation, etc., even if the superconducting connections 1124 are in the irradiation area of the treatment head 1111, the superconducting connections 1124 may prevent the superconducting magnets from losing superconductivity due to radiation.

In some embodiments, the superconducting magnets may be kept under a low working temperature (e.g., approximately 4.2 K) using a coolant free cooling technique. By using the liquid helium-free refrigeration technique, the risk of loss of the superconductivity of the superconducting magnets 1121 during rotation can be further avoided. Moreover, using the liquid helium-free refrigeration technique may significantly reduce the weight of the superconducting magnets and simplify the structure of the MRI device 1120. More descriptions for the coolant free cooling technique may be found elsewhere in the present disclosure (e.g., FIGS. 2-4 and the descriptions thereof).

It should be noted that the above description of the medical device 1100 is merely provided for the purposes of illustration, and not intended to limit the scope of the present disclosure. For persons having ordinary skills in the art, multiple variations and modifications may be made under the teachings of the present disclosure. For example, the arrangement of the assemblies and/or functions of the medical device 1100 may be varied or changed according to specific implementation scenarios.

Figure 14:
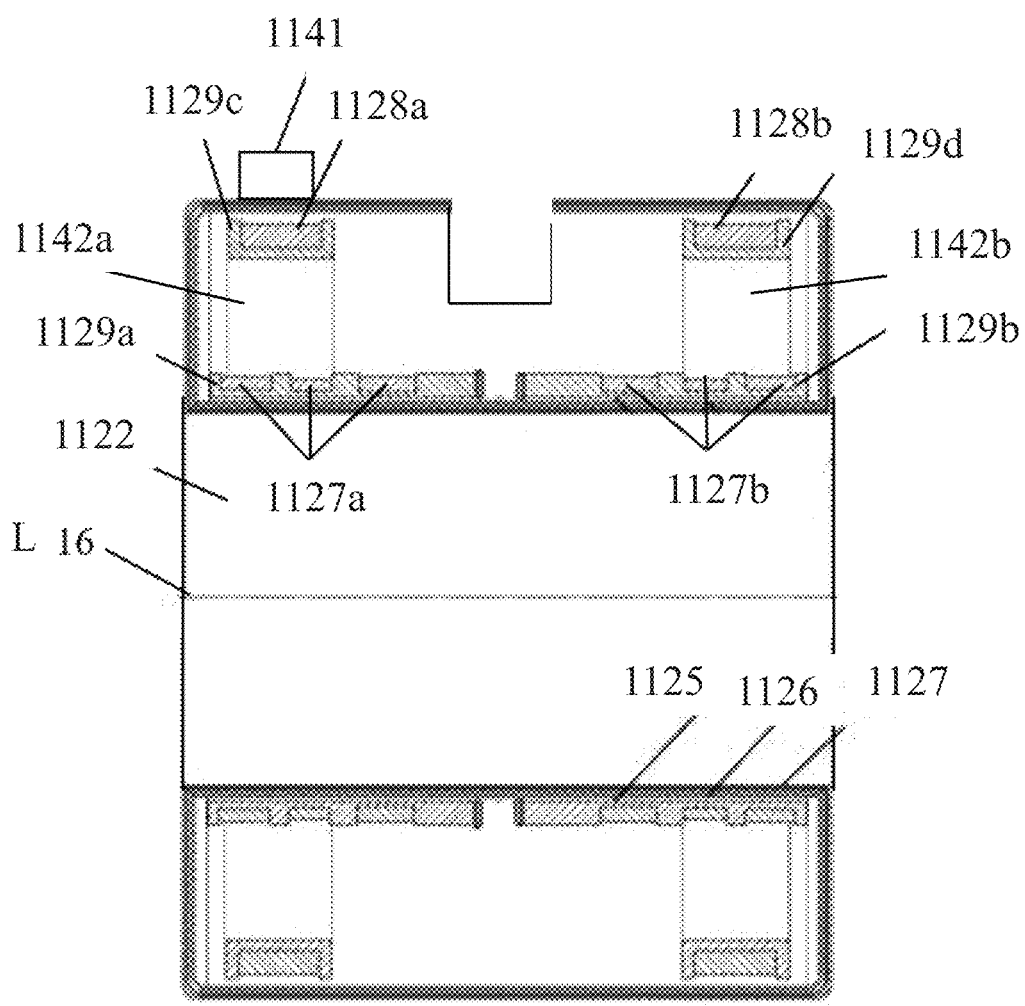
FIG. 14 is a sectional view illustrating an exemplary MRI device according to some embodiments of the present disclosure.

FIG. 14 is a sectional view illustrating an exemplary MRI device according to some embodiments of the present disclosure. FIG. 14 shows the sectional view of the MRI device 1120 in a plane parallel with the Z-axis L of the main body of the MRI device 1120 as shown in FIG. 11.

As described in FIG. 11, the MRI device 1120 may include a cooling assembly configured to cool the one or more superconducting magnets without using a coolant (also referred to as a coolant free cooling technique) to keep the one or more superconducting magnets under a low working temperature (e.g., approximately 4.2 K). The cooling assembly may include one or more refrigerators and one or more heat conductors physically connecting the one or more refrigerators and the one or more superconducting magnets.

For example, the cooling assembly may include one or more refrigerators 1141. Each of the one or more refrigerators may include a cold head configured to provide refrigeration to the one or more superconducting magnets via the one or more heat conductors.

In some embodiments, the MRI device 1120 may include a cryostat including an inner vessel, an outer vessel encompassing the inner vessel, and a thermal shielding layer configured between the outer vessel and the inner vessel. The inner vessel may be configured to accommodate one or more superconducting magnets 1421 and a coolant (e.g., liquid helium). The coolant may be configured to keep the one or more superconducting magnets that are located in the cryostat under a low working temperature (e.g., approximately 4.2 K). The inner vessel may also be referred to as a liquid helium container. The outer vessel may include a vacuum container.

As shown in FIG. 14, the superconducting magnets may include one or more main coils and one or more shielding coils. In some embodiments, the main coils may include a first main coil 1127a and a second main coil 1127b. The shielding coils may include a first shielding coil 1128a and a second shielding coil 1128b. The first main coil 1127a and a second main coil 127b may be electronically connected through, for example, one or more superconducting connections. The direction of current in the shielding coils (i.e., the first shielding coil 1128a and the second shielding coil 1128b) may be opposite to the direction of current in the main coils (i.e., the first main coil 1127a and the second main coil 1127b), and the magnetic field generated by the shielding coils may have an opposite direction to the fringing magnetic field generated by the main coils, such that the fringing magnetic field generated by the main coils may be canceled out by the magnetic field generated by the shielding coils. The inner diameter of each of the shielding coils may be larger than the outer diameter of each of the main coils. The main coils and the shielding coils may be separated or connected respectively. For example, the first main coil 1127a may be electrically connected with the second main coil 1127b via one or more first superconducting connections. As another example, the first shielding coil 1128a may be electrically connected with the second shielding coil 1128b via one or more second superconducting connections. As still another example, the first main coil 1127a may be separated from the second main coil 1127b; and the first shielding coil 1128a may be separated from the second shielding coil 1128b.

In some embodiments, the first main coil 1127a and the second main coil 1127b may be wound on a first bobbin 1129a and a second bobbin 1129b, respectively. When current passes through the first main coil 1127a and the second main coil 1127b, a magnetic field may be generated in the bore 1122, and the direction of the magnetic field in the bore 1122 may be parallel to the axis L. The strength of the magnetic field generated by the first main coil 1127a and the second main coil 1127b may be related to the number (or count) of turns of the main coils. The first shielding coil 1128a and the second shielding coil 1128b may be wound on a third bobbin 1129c and a fourth bobbin 1129d, respectively.

In some embodiments, at least one of the bobbins (e.g., the first bobbin 1129a, the second bobbin 1129b, the third bobbin 1129c, and the fourth bobbin 1129d) may be provided with a groove and/or a heat conduction pipe for accommodating a coolant (e.g., liquid helium). The groove may be sealed to form a sealed cavity to accommodate the coolant. In some embodiments, the coolant may absorb heat generated by the coils (e.g., the main coils and the shielding coils). The heated coolant may be cooled by the one or more refrigerators. For example, the one or more refrigerators may include a cold heat that is configured to provide refrigeration to the groove and/or the heat conduction pipe via the one or more heat conductors that are thermally connected with the groove and/or the heat conduction pipe.

In some embodiments, the MRI device 1120 may further include a heat exchange plate 1125, a thermal shielding layer 1126, and a vacuum layer 1127. The vacuum layer 1127 may also be referred to as a vacuum container. The vacuum layer 1127 may encompass the heat exchange plate 1125 and the thermal shielding layer 1126 may be located between the heat exchange plate 1125 and the vacuum layer 1127. The descriptions regarding the thermal shielding layer, the heat exchange plate, and the vacuum layer may be found elsewhere in the present disclosure. See, FIG. 6 and relevant descriptions thereof.

It should be noted that the above description of the MRI device 1120 is merely provided for the purposes of illustration, and not intended to limit the scope of the present disclosure. For persons having ordinary skills in the art, multiple variations and modifications may be made under the teachings of the present disclosure. For example, the arrangement of the assemblies and/or functions of the MRI device 1120 may be varied or changed according to specific implementation scenarios. As another example, the main body of the MRI device 1120 may include a groove configured to accommodate a portion of a radiotherapy device.

Figure 15:
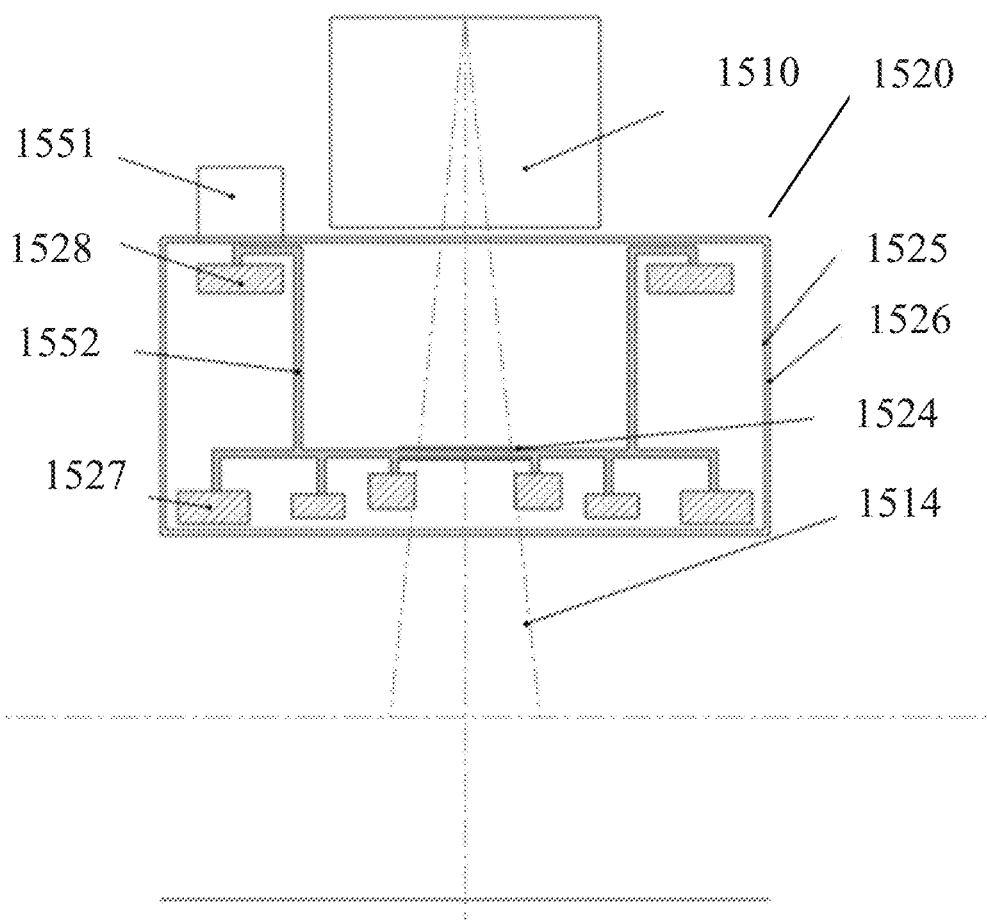
FIG. 15 is a schematic diagram illustrating a sectional view of an exemplary medical device according to some embodiments of the present disclosure.

FIG. 15 is a schematic diagram illustrating a sectional view of an exemplary medical device according to some embodiments of the present disclosure. The medical device 1500 may be an exemplary embodiment of the medical device 110. The following descriptions are provided regarding the medical device including an MRI device and a radiotherapy device unless otherwise stated. It should be noted that the descriptions of the MRI device and the radiotherapy device in the present disclosure are merely provided for illustration, and not intended to limit the scope of the present disclosure. The MRI device and the radiotherapy device may be similar to the MRI device 1120 and the radiotherapy device 1110 as described in FIG. 11. For example, the MRI device may include one or more superconducting magnets that include one or more main coils 1527 and one or more shielding coils 1528. As another example, the MRI device may include a thermal shielding layer 1525 and a vacuum layer 1526. As still another example, the one or more main coils 1527 may be electrically connected via one or more superconducting connections 1524.

Different from the medical device 1100, the radiotherapy device 1510 may be located independently from the MRI device 1520. For example, the treatment head of the radiotherapy device 1510 may be located outside of the main body of the MRI device 1520. In some embodiments, the radiotherapy device 1510 and the MRI device 1520 may rotate simultaneously. In some embodiments, the radiotherapy device 1510 may rotate independently relative to the MRI device 1520.

In some embodiments, the superconducting magnets in FIG. 15 may be kept in a low-temperature using a coolant free cooling technique for the normal working of the MRI device.

As shown in FIG. 15, the MRI device may include a cooling assembly configured to cool the one or more superconducting magnets. The cooling assembly may include a refrigerator 1551 and heat conductors 1552 physically connecting the refrigerators 1551 and the one or more superconducting magnets (e.g., the main coils 1527 and the shielding coils 1528). For example, each of the heat conductors 1552 located at two sides of the superconducting connections 1524 may be connected with one of the main coils 1527 with one of the shielding coils 1528 located at the same side of the two sides of the superconducting connections 1524. The refrigerator 1551 may be thermally connected with one of the heat conductors 1552.

In some embodiments, in order to prevent the superconducting connections from being irradiated, the main body of the MRI device 220 may be provided with one or more protection components. At least part of the superconducting connections 1524 may locate in the protection components. For example, the superconducting connections 1524 which located in the potential irradiation area of the radiation beams may be located in the protection components. In some embodiments, the protection components may include a tubular structure and one of the one or more superconducting connections 1524 may be arranged in the tubular structure. In some embodiments, at least one of the protection components may be a hollow cylindrical structure (as shown in FIG. 12). In some embodiments, at least one of the protection components may be a hollow triangular prism structure (as shown in FIG. 13). In some alternative embodiments, at least one of the protection components may be a quadrangular prism structure, a pentagonal prism structure, or the like. Since the protection components have the functions of shielding radiation beams, thermal insulation, etc., even if the superconducting connections 1524 are in the irradiation area of the treatment head of the radiotherapy device, the superconducting connections 1524 may prevent the superconducting magnets from losing superconductivity due to radiation. In some embodiments, the arrangement of the protection components can prevent the radiation beams from irradiating the heat conductors to cause the temperature to rise, thereby causing the magnet to quench.

It should be noted that the above description regarding FIGS. 1-15 are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the protection components may be one or more other additional components not described and/or without one or more of the operations discussed above.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±1%, ±5%, ±10%, or ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A system, comprising: a magnetic resonance imaging (MRI) device including:
    a main body including a bore that is configured to accommodate a subject, wherein the main body includes a first portion and a second portion spaced apart from each other, a first side surface of the first portion and a second side surface of the second portion face each other, and a space is formed between the first side surface and the second side surface;
    multiple superconducting magnets accommodated in the two portions of the main body and configured to generate a magnetic field in the bore;
    a radiation source configured to emit a radiation beam toward the bore through the space;
    one or more superconducting connections each of which is configured to connect at least two of the multiple superconducting magnets, wherein the one or more superconducting connections are located on the outside of the superconducting magnets, and
    one or more protection components configured to protect the one or more superconducting connections, wherein
    the one or more superconducting connections and the one or more protection components are located in the space;
    a first end of each protection component is mechanically connected to a part of the first side surface, and a second end of each protection component is mechanically connected to a part of the second side surface; and
    the one or more protection components are capable of shielding the radiation beam and each of the one or more superconducting connections is arranged within one of the one or more protection component such that the radiation beam in the space is shielded by the one or more protection component and prevented from irradiating the one or more superconducting connections in the space;
    the MRI device further includes a heat exchange plate, a thermal shielding layer, and a vacuum layer arranged around the superconducting magnets successively along a direction perpendicular to an axial direction of the MRI device,
    the heat exchange plate is configured to exchange heat with the superconducting magnets,
    the thermal shielding layer is configured to prevent heat exchange between the vacuum layer and the heat exchange plate, and
    the vacuum layer is configured to prevent heat exchange between the outside of the vacuum layer and the inside of the vacuum layer.

2. The system of claim 1, wherein the protection components includes one or more tubular structures, each of the one or more superconducting connections is arranged in one of the one or more tubular structures, a first end of each tubular structure is mechanically connected to a part of the first side surface, and a second end of each tubular structure is mechanically connected to a part of the second side surface.

3. The system of claim 1, wherein a direction of the radiation beam is perpendicular to the direction of the magnetic field.

4. The system of claim 1, wherein
    the radiation source includes a treatment radiation source in a radiotherapy device.

5. The system of claim 1, further comprising:
    a cooling assembly configured to cool the one or more superconducting magnets, the cooling assembly including one or more refrigerators and one or more heat conductors thermally connecting the one or more refrigerators and the one or more superconducting magnets.

6. The system of claim 1, wherein at least a portion of the radiation source is located in the space, and the radiation source is able to rotate in the plane perpendicular to a direction of the magnetic field in the space.

7. The system of claim 1, wherein the heat exchange plate includes a heat exchanger formed by stacking a series of metal sheets, and a rectangular channel is formed between the series of metal sheets for heat exchange.

8. The system of claim 1, wherein the MRI device includes a treatment head including the radiation source, a distance between the treatment head and a center point of the bore is in a range of 40-60 centimeters, and the treatment head is moveable to adjust the distance between the treatment head and the center point of the bore.

9. The system of claim 2, wherein for each of the one or more tubular structures, a diameter of the tubular structure is smaller than a diameter of the bore, and the tubular structure is integrally located on one side of a central axis of the bore.

10. The system of claim 1, wherein the material of the one or more protection components include at least one of lead and tungsten.

11. The system of claim 1, wherein the one or more protection components include a radiation shielding layer configured for shielding the radiation beam and a thermal insulation layer configured for heat preservation and heat insulation, an attenuation coefficient of the radiation shielding layer is greater than a 1000/cm, and a thermal conductivity of the thermal insulation layer is less than 20 W/m·K.

12. A system, comprising: a magnetic resonance imaging (MRI) device including:
a main body including a bore that is configured to accommodate a subject, wherein the main body includes a first portion and a second portion spaced apart from each other, a first side surface of the first portion and a second side surface of the second portion face each other, and a space is formed between the first side surface and the second side surface;
multiple superconducting magnets accommodated in the two portions of the main body around the bore configured to generate a magnetic field in the bore;
a cooling assembly configured to cool the one or more superconducting magnets without immersing the one or more superconducting magnets in a coolant, the cooling assembly including one or more refrigerators and one or more heat conductors, the one or more heat conductor thermally connecting the one or more refrigerators and the one or more superconducting magnets;
a radiation source configured to emit a radiation beam toward the bore through the space, the radiation source and the cooling assembly being able to simultaneously rotate with a rotation of the MRI device;
one or more superconducting connections each of which is configured to connect at least two of the multiple superconducting magnets, wherein the one or more superconducting connections are located on the outside of the superconducting magnets;
one or more protection components configured to protect the one or more superconducting connections, wherein the one or more superconducting connections and the one or more protection components are located in the space;
a first end of each protection component is mechanically connected to a part of the first side surface, and a second end of each protection component is mechanically connected to a part of the second side surface; and
the one or more protection components are capable of shielding the radiation beam and each of the one or more superconducting connections is arranged within one of the one or more protection components such that the radiation beam in the space is shielded by the one or more protection components and prevented from irradiating the one or more superconducting connections in the space.

13. The system of claim 12, wherein the main body further includes:
a channel on a shell of the main body along a direction substantially perpendicular to a direction of the magnetic field in the bore, and
at least a portion of the radiation source is disposed in the channel, the radiation beam passing through the channel to the bore.

14. The system of claim 13, wherein:
the shell of the main body includes an inner wall and an outer wall,
the outer wall is configured with a first through hole and the inner wall is configured with a second through hole, and
a diameter of the first through hole exceeds a diameter of the second through hole, the channel being formed by the first through hole and the second through hole.

15. The system of claim 12, wherein each of the superconducting magnets includes a main coil and a shielding coil, the main coils of the superconducting magnets are electrically connected via one or more first superconducting connections, and the shielding coils of the superconducting magnets are electrically connected by one or more second superconducting connections.

16. The system of claim 15, wherein
the one or more refrigerators include one single refrigerator that is thermally connected with the main coil and the shielding coil of one of the superconducting magnets via one of the one or more heat conductors.

17. The system of claim 16, wherein
one of the main coils of the superconducting magnets thermally connects to another one of the main coils of the superconducting magnets;
one of the shielding coils of the superconducting magnets thermally connects to another one of the shielding coils of the superconducting magnets; and
the main coil and the shielding coil of another one of the superconducting magnets thermally connect via one of the heat conductors.

18. The system of claim 15, wherein
a count of the one or more refrigerators equals 2, and
each of the one or more refrigerators is thermally connected with the main coil and the shielding coil in one of the one or more superconducting magnets through one of the one or more heat conductors.

19. The system of claim 15, wherein each of the one or more protection components is configured to prevent at least a portion of the radiation beam from irradiating at least one of the one or more first superconducting connections or the one or more second superconducting connections.

* * * * *